(12) United States Patent
Ward et al.

(10) Patent No.: US 11,207,564 B2
(45) Date of Patent: Dec. 28, 2021

(54) INTERACTIVE EXERCISE MACHINE SYSTEM WITH MIRROR DISPLAY

(71) Applicant: Interactive Strength, Inc., Carson City, NV (US)

(72) Inventors: Trent Ward, London (GB); Gregor Angus Berkowitz, San Francisco, CA (US); Roland Jeffrey Wyatt, Bozeman, MT (US); Yves Albert Behar, San Francisco, CA (US)

(73) Assignee: Interactive Strength, Inc., Carson City, NV (US)

( * ) Notice: Subject to any disclaimer, the term of this patent is extended or adjusted under 35 U.S.C. 154(b) by 0 days.

(21) Appl. No.: 16/534,158

(22) Filed: Aug. 7, 2019

(65) Prior Publication Data

US 2020/0047030 A1 Feb. 13, 2020

Related U.S. Application Data

(60) Provisional application No. 62/740,184, filed on Oct. 2, 2018, provisional application No. 62/715,591, filed on Aug. 7, 2018.

(51) Int. Cl.
*A63B 24/00* (2006.01)
*A61B 5/11* (2006.01)
(Continued)

(52) U.S. Cl.
CPC ........ *A63B 24/0087* (2013.01); *A61B 5/0205* (2013.01); *A61B 5/1114* (2013.01);
(Continued)

(58) Field of Classification Search
CPC ............ A63B 24/0087; A63B 71/0054; A63B 24/0021; A63B 21/153; A63B 24/0062;
(Continued)

(56) References Cited

U.S. PATENT DOCUMENTS

| 4,804,179 A | 2/1989 | Murphy |
| 5,090,694 A * | 2/1992 | Pauls ................... A63B 21/015 |
| | | 482/118 |

(Continued)

FOREIGN PATENT DOCUMENTS

| WO | WO1993000970 A1 | 6/1992 |
| WO | WO2013180651 A1 | 5/2013 |
| WO | 2018104084 | 6/2018 |

OTHER PUBLICATIONS

"Mirror" (Mirror) Oct. 17, 2019 https://www.mirror.co/; entire document.

(Continued)

*Primary Examiner* — Sundhara M Ganesan
*Assistant Examiner* — Shila Jalalzadeh Abyaneh
(74) *Attorney, Agent, or Firm* — David R. Stevens; Stevens Law Group

(57) ABSTRACT

An interactive exercise system includes a mechanical support system and a display module held by the mechanical support system. A mirror element is attached to at least partially cover the display module. At least one movable arm is connected to the support system and at least one force-controlled component is connected to the mechanical support system. The force-controlled component can be graspable by a user and allows for a range of exercise types and programs.

13 Claims, 24 Drawing Sheets

(51) Int. Cl.
  *A61B 5/0205* (2006.01)
  *A63B 21/00* (2006.01)
  *G06F 3/048* (2013.01)
  *G06F 3/01* (2006.01)
  *G06F 3/03* (2006.01)
  *G06K 9/00* (2006.01)
  *A63F 13/213* (2014.01)
  *A61B 5/00* (2006.01)
  *A63B 71/06* (2006.01)
  *A63F 13/28* (2014.01)
  *A63B 21/005* (2006.01)
  *A63B 71/00* (2006.01)

(52) U.S. Cl.
  CPC ............ *A61B 5/1126* (2013.01); *A61B 5/486* (2013.01); *A63B 21/0058* (2013.01); *A63B 21/153* (2013.01); *A63B 21/4035* (2015.10); *A63B 24/0006* (2013.01); *A63B 24/0021* (2013.01); *A63B 24/0062* (2013.01); *A63B 24/0075* (2013.01); *A63B 71/0054* (2013.01); *A63B 71/0622* (2013.01); *A63F 13/213* (2014.09); *A63F 13/28* (2014.09); *G06F 3/011* (2013.01); *G06F 3/016* (2013.01); *G06F 3/0304* (2013.01); *G06F 3/048* (2013.01); *G06K 9/00342* (2013.01); *G06K 9/00369* (2013.01); *A63B 2024/0012* (2013.01); *A63B 2024/0015* (2013.01); *A63B 2024/0025* (2013.01); *A63B 2024/0068* (2013.01); *A63B 2024/0093* (2013.01); *A63B 2071/0072* (2013.01); *A63B 2071/065* (2013.01); *A63B 2071/0647* (2013.01); *A63B 2071/0658* (2013.01); *A63B 2220/51* (2013.01); *A63B 2220/806* (2013.01); *A63B 2220/833* (2013.01); *A63B 2225/12* (2013.01); *A63B 2225/15* (2013.01); *A63B 2225/20* (2013.01); *A63B 2225/50* (2013.01); *A63B 2230/06* (2013.01); *A63B 2230/42* (2013.01)

(58) Field of Classification Search
  CPC ............ A63B 71/0622; A63B 24/0006; A63B 24/0075; A63B 2071/0072; A63B 2071/0658; A63B 2024/0015; A63B 2024/0025; A63B 2225/15; A63B 2071/0647; A63B 2071/065; A63B 2220/833; A63B 2225/50; A63B 2024/0068; A63B 2024/0093; A63B 2220/51; A63B 2220/806; A63B 2225/20; A63B 2230/06; A63B 2230/42; A63B 2024/0012; A63B 2225/12; A63B 2024/0096; A63B 2071/024; A63B 2220/802; A63B 2225/093; A63B 2220/89; A63B 2220/80; A63B 2071/063; A63B 2210/50; A63B 2220/12; A63B 2220/808; A63B 2230/062; A63B 2230/50; A63B 2220/54; A63B 2230/425; A63B 2220/40; A63B 21/4035; A63B 21/0058; G06K 9/00369; G06K 9/00342; G06K 9/00671; G06K 9/2018; G06F 3/048; G06F 3/011; G06F 3/0304; G06F 3/016; G06F 3/017; G06F 3/0346; A61B 5/1114; A61B 5/1126; A61B 5/486; A61B 5/0205; A61B 5/6895; A61B 5/7435; A61B 5/744; A61B 5/7267; A61B 5/0022; A61B 5/0816; A61B 5/024; A61B 5/01; A61B 5/1128; A61B 5/113; G16H 40/67

See application file for complete search history.

(56) References Cited

U.S. PATENT DOCUMENTS

| | | | |
|---|---|---|---|
| 5,569,138 A * | 10/1996 | Wang | A63B 21/015 |
| | | | 482/120 |
| 5,577,981 A | 11/1996 | Jarvik | |
| 5,690,582 A | 11/1997 | Ulrich | |
| 5,846,086 A | 12/1998 | Bizzi | |
| 6,443,877 B1 * | 9/2002 | Hoecht | A63B 23/035 |
| | | | 482/103 |
| 7,018,211 B1 | 3/2006 | Birkhölzer | |
| 7,172,538 B2 * | 2/2007 | Keiser | A63B 21/0087 |
| | | | 482/140 |
| 7,625,316 B1 | 12/2009 | Amsbury | |
| 7,780,450 B2 | 5/2010 | Tarry | |
| 8,328,691 B2 | 12/2012 | Lanfermann | |
| 8,845,499 B1 | 9/2014 | Boatwright | |
| 9,015,638 B2 | 4/2015 | Kipman | |
| 9,821,224 B2 | 11/2017 | Latta | |
| 10,441,840 B2 * | 10/2019 | Dalebout | A63B 21/4043 |
| 10,500,442 B2 * | 12/2019 | Hong | A63B 21/018 |
| 10,668,320 B2 * | 6/2020 | Watterson | A63B 23/1209 |
| 10,918,899 B2 * | 2/2021 | Gisin | A63B 21/4047 |
| 2003/0045406 A1 * | 3/2003 | Stone | A63B 21/154 |
| | | | 482/100 |
| 2006/0103627 A1 | 5/2006 | Watanabe | |
| 2006/0189457 A1 * | 8/2006 | Ripley | A63B 21/0628 |
| | | | 482/99 |
| 2007/0219051 A1 | 9/2007 | Hayashino | |
| 2008/0051256 A1 * | 2/2008 | Ashby | A63B 23/12 |
| | | | 482/5 |
| 2008/0051263 A1 | 2/2008 | Rasmussen | |
| 2010/0281432 A1 | 11/2010 | Geisner | |
| 2011/0098155 A1 | 4/2011 | Lemos | |
| 2012/0021876 A1 * | 1/2012 | Hsiung | A63B 21/0628 |
| | | | 482/93 |
| 2013/0145272 A1 | 6/2013 | Boggie | |
| 2013/0171600 A1 | 7/2013 | Yuasa | |
| 2013/0171601 A1 * | 7/2013 | Yuasa | A61B 5/744 |
| | | | 434/258 |
| 2013/0190143 A1 | 7/2013 | Greenhill | |
| 2014/0038777 A1 | 2/2014 | Bird | |
| 2014/0141950 A1 | 5/2014 | Greiwe | |
| 2014/0194250 A1 * | 7/2014 | Reich | A63B 24/0062 |
| | | | 482/5 |
| 2014/0276095 A1 | 9/2014 | Griggs | |
| 2015/0038300 A1 * | 2/2015 | Forhan | A63B 21/156 |
| | | | 482/72 |
| 2015/0099252 A1 | 4/2015 | Anderson | |
| 2015/0111698 A1 | 4/2015 | Abbondanza | |
| 2015/0196804 A1 | 7/2015 | Koduri | |
| 2015/0196805 A1 * | 7/2015 | Koduri | A63B 24/0062 |
| | | | 482/6 |
| 2016/0067548 A1 * | 3/2016 | Shiao | A63B 24/0087 |
| | | | 482/5 |
| 2016/0089573 A1 | 3/2016 | House | |
| 2016/0093081 A1 | 3/2016 | Kim | |
| 2016/0158603 A1 * | 6/2016 | Darwood | A63B 21/0058 |
| | | | 482/5 |
| 2016/0256740 A1 | 9/2016 | Rowe | |
| 2016/0284132 A1 | 9/2016 | Kim | |
| 2017/0014684 A1 | 1/2017 | Burroughs | |
| 2017/0056726 A1 * | 3/2017 | Dalebout | A61B 5/11 |
| 2017/0076629 A1 | 3/2017 | Kim | |
| 2017/0100637 A1 | 4/2017 | Princen | |
| 2017/0173396 A1 | 6/2017 | Lu | |
| 2017/0246507 A1 | 8/2017 | Kennington | |
| 2017/0282015 A1 | 10/2017 | Wicks | |
| 2017/0312582 A1 | 11/2017 | Root | |
| 2018/0021616 A1 | 1/2018 | Orady | |
| 2018/0021627 A1 | 1/2018 | Deluca | |
| 2018/0126248 A1 | 5/2018 | Dion | |

(56) References Cited

U.S. PATENT DOCUMENTS

| | | |
|---|---|---|
| 2018/0214729 A1 | 8/2018 | Rubin |
| 2019/0099652 A1* | 4/2019 | Orady ................... A63B 23/12 |
| 2019/0126090 A1* | 5/2019 | O'Connor .......... A63B 24/0087 |
| 2020/0014967 A1* | 1/2020 | Putnam ................ A61B 5/0079 |
| 2020/0139187 A1* | 5/2020 | Kennington ........... A63B 23/12 |
| 2020/0376318 A1* | 12/2020 | Durket ............... A63B 21/4034 |

OTHER PUBLICATIONS

Mirror raises $13 million for virtual fitness classes, Katie Roof, https://techcrunch.com/2018/02/06/mirror-raises-13-million-for-virtual-fitness-classes/.

This Startup Wants You to Trade Your Gym Membership for a Mirror, Michelle Cheng, https://www.inc.com/michelle-cheng/this-startup-is-building-a-smart-mirror-that-will-make-you-break-a-sweat.html.

* cited by examiner

1000A

1000B

PERSONAL PROFILE

ENCOURAGE & PUSH

ADAPTIVE PROGRAMS

REAL-TIME DATA

INTERACTIVE EXERCISE MACHINE SYSTEM WITH MIRROR DISPLAY

RELATED APPLICATIONS

This application claims the benefit of U.S. Provisional Application Ser. No. 62/715,591 filed Aug. 7, 2018 and U.S. Provisional Application Ser. No. 62/740,184 filed Oct. 2, 2018, which are hereby incorporated herein by reference in their entirety for all purposes.

TECHNICAL FIELD

The present disclosure relates to an interactive exercise machine. In one embodiment, a mirrored display is used to present both a user's reflection and exercise training videos or graphics. A stereo or three-dimensional camera system can also be used to continuously or non-continuously monitor body position, providing data needed to interactively adjust machine force profiles, provide feedback to users, and track for improved results, improvement in form, and prevention of injury.

BACKGROUND

Exercise machines that include handgrips connected by cables to weights or resistant loads are widely used. Such machines allow for various training exercises by a user and can be configured to present a range of force profiles. However, for best results and to reduce chance of muscle damage, many exercises require correct performance of complex actions by the user during an exercise routine and skilled adjustment of weights or force resistance. Novice or casual users often do not have the knowledge or ability to correctly practice an exercise routine or make changes to the exercise machine configuration. Unfortunately, many users do not have the time and/or motivation to visit exercise facilities; cannot afford to pay for personal trainers familiar with the exercise machine or membership in exercise facilities with skilled monitoring personnel.

SUMMARY

In one embodiment, an interactive exercise system includes a mechanical support system, a display module held by the mechanical support system, and a mirror element attached to at least partially cover the display module. At least one movable arm is connected to the mechanical support system with the movable arm further including at least one force-controlled component engageable or graspable by a user and connected to the mechanical support system.

In some embodiments the display module provides video and a three-dimensional camera system can be directed to monitor user position. Such systems allow interactive graphics based at least in part on data provided through a three-dimensional camera.

In other embodiments, a force applied through the force-controlled component is based at least in part on detected user input. The force applied through the force-controlled component can also be based at least in part on real time analysis of at least one of user position, user applied force, and user biometric signals.

In one embodiment, the interactive exercise system includes a biometric signal analysis module able to detect at least one of heart rate and breath rate and based on the biometric signal modify force applied through the force-controlled component.

In one embodiment, the interactive exercise system includes an exercise catalog module to allow selection of specific exercises. These exercises can be developed by expert trainers, other users, or created by a user. In some embodiments the exercises can be provided via a personal exercise history module able to store exercise history, including at least one of three-dimensional user pose, video of user, and skeletal extraction data.

In one embodiment an audio module is configured to allow at least one of user voice control, receipt of audio instructions by a user, and music.

In one embodiment, a method for displaying an exercise program on a display module having a mirror element at least partially covering the display module is described. At least one sensor can be used to sense an image of the user. At least one force feedback controlled movable arm can be used to gather user related force data and at least one sensor used to gather biometric data associated with the user (including but not limited to force sensor data from the movable arm). User related force data, biometric data, and image of the user can be analyzed, and training feedback based on the analysis provided to the user or other returned to permit adjustment of the exercise program.

In one embodiment the image used in the described method embodiment includes at least one of still image data and video data. The method can use information from multiple sensor systems, including at least one from a sensor is selected from the group consisting of a stereo camera, a structured light camera, an infrared camera, and a 2D camera.

In one embodiment the biometric data includes a heart rate of the user. In another embodiment, biometric data can be used to calculate or estimate energy burned by the user. Analyzing the biometric data and the image of the user can occur in real time.

In one embodiment skeletal and/or joint data can be extracted from the image of the user, allowing presentations to the user that can improve posture or exercise position.

BRIEF DESCRIPTION OF THE DRAWINGS

Non-limiting and non-exhaustive embodiments of the present disclosure are described with reference to the following figures, wherein like reference numerals refer to like parts throughout the various figures unless otherwise specified.

FIG. 2I illustrates a floor mounted interactive exercise machine;

DETAILED DESCRIPTION

Figure 1:
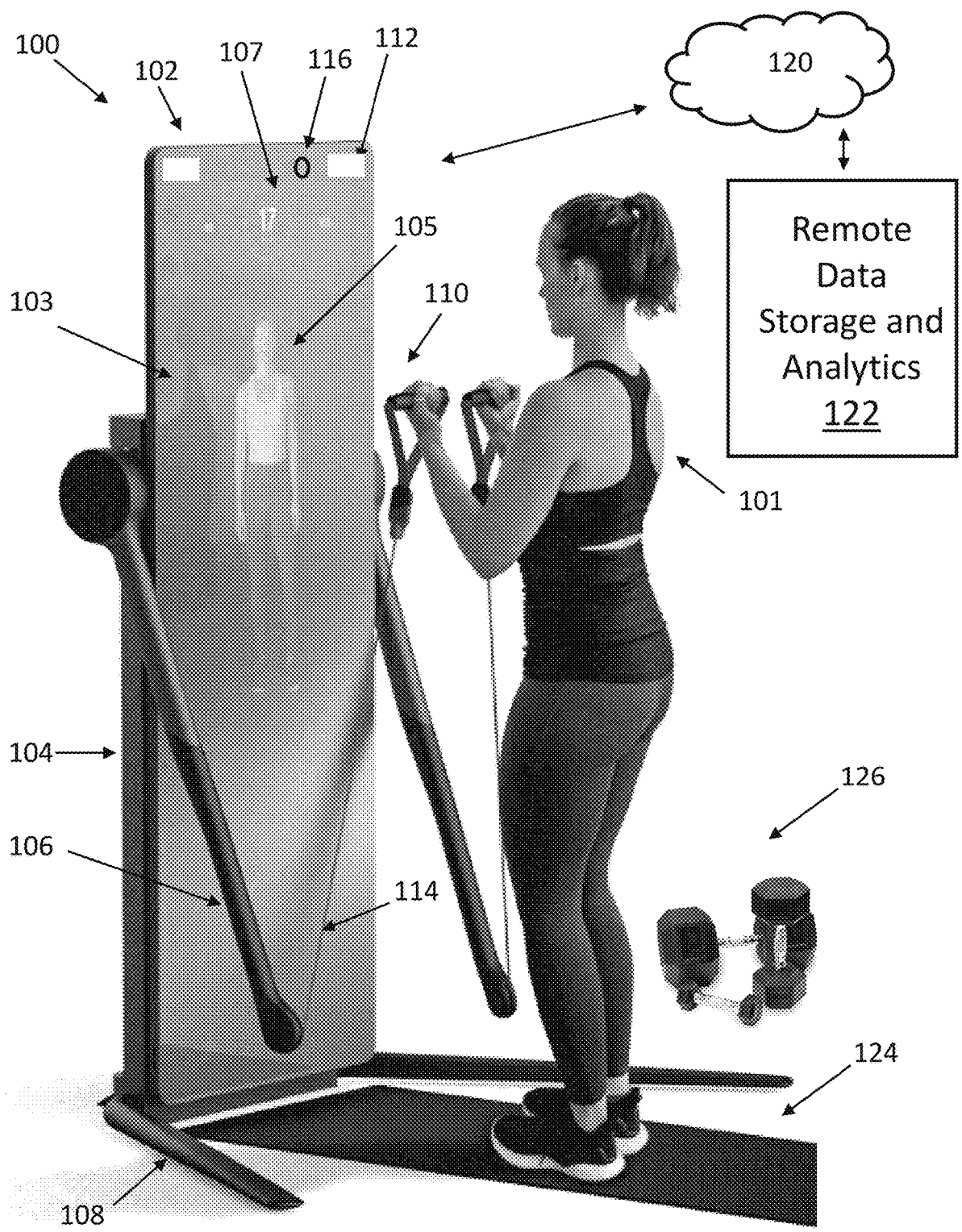
FIG. 1 illustrates an interactive exercise machine system.

For best results and to reduce chance of muscle damage, many exercises require correct performance of complex actions by the user during an exercise routine and skilled adjustment of weights or force resistance. Novice or casual users often do not have the knowledge or ability to correctly practice an exercise routine or make changes to the exercise machine configuration. Unfortunately, many users cannot afford to pay for personal trainers familiar with the exercise machine or membership in exercise facilities with skilled monitoring personnel. FIG. 1 is an illustration of one embodiment of an interactive exercise machine system 100 with personalized training capabilities being used by a user 101. The system 100 includes an exercise machine display 102 held by a mechanical support system 104. The display 102 can be at least partially covered with a semi-reflective coating or mirror that reflects an image 103 of the user 101, while still allowing viewing of videos 105 or information 107 presented by the display 102.

Movable arms 106 and legs 108 are attached to the mechanical support system 104. User engageable components such as graspable handles 110 are connected to force sensor 114 with monitored cords extending through the movable arms 106. This arrangement allows for providing an actively adjustable, force sensor monitored, variable resistant force, to a user 101 engaged in exercise. One or more cameras 112 can be used to monitor user position, with user position data being usable to allow for adjustment of graspable handle 110 usage force. In some embodiments, a range of environmental or other sensors 116 can be available, including audio sensors, microphones, ambient light level sensors, geo-positioning system (GNSS/GPS) data, accelerometer data, yaw, pitch and roll data, chemical sensor data (e.g. carbon monoxide levels), humidity, and temperature data. In one embodiment, wireless connection can be made to sensor equipped external exercise equipment, including a pressure sensor mat 124 or accelerometer/gyroscope/force sensor equipped weights, balls, bars, tubes, balance systems, stationary or moveable or other exercise devices 126.

In operation, user position and force sensor data be locally stored or provided (via connected network cloud 120) to a remote data storage and analytics service 122. A network cloud 120 can include, but is not limited to servers, desktop computers, laptops, tablets, or smart phones. Remote server embodiments may also be implemented in cloud computing environments. Cloud computing may be defined as a model for enabling ubiquitous, convenient, on-demand network access to a shared pool of configurable computing resources (e.g., networks, servers, storage, applications, and services) that can be rapidly provisioned via virtualization and released with minimal management effort or service provider interaction, and then scaled accordingly. A cloud model can allow for on-demand self-service, broad network access, resource pooling, rapid elasticity, measured service or various service models (e.g., Software as a Service ("SaaS"), Platform as a Service ("PaaS"), Infrastructure as a Service ("IaaS"), and deployment models (e.g., private cloud, community cloud, public cloud, hybrid cloud, etc.).

Based on user requirements, stored, cached, streamed or live video can be received by exercise machine display 102.

In some embodiments, augmented reality graphics can be superimposed on the user image 103 to provide guidance for improving user position as monitored by the cameras and other sensors 112. In other embodiments, force sensor information can be used to provide real-time or near real-time adjustments to resistant force profiles, workout routines, or training schedules.

In the illustrated embodiment of FIG. 1, the display includes an LCD television display. Alternatively, in other embodiments the display can be an OLED display or a projected display. The display can be sized to approximately match size of a user, while in other embodiments it can be sized to range anywhere from 0.5× to 2× user size. Typically, the display 102 is positioned to be slightly higher than a user and extends downward to a floor. A partially silvered mirror can be adhesively attached or positioned in overlaying proximity to the display 102. The amount of mirror reflection is set to allow simultaneous viewing of the user 101 image and information provided by display 102. The display can present information related to a user, including exercise machine usage information, training videos, current or historical exercise related data, interactive simulated or live person video for training or encouragement, entertainment videos, social network related information or communications, or advertisements.

The cameras 112 can include a plurality of video cameras to provide multiple video feeds of the exercise machine environment and user. Cameras can be mounted on the front, side, top, arms, or legs of the exercise machine. In an alternative embodiment, one or more cameras 112 can be mounted separately from the exercise machine to provide a more complete view of the user, including top, side, and behind views of the user. In some embodiments, cameras can be grouped into clusters, with multiple cameras pointed to provide separated and slightly overlapping fields of view. The three-dimensional cameras can provide absolute or relative distance measurements with respect to user position. In some embodiments three-dimensional cameras can include stereo cameras or cameras used in conjunction with structured lighting. In some embodiments, infrared, UV, or hyperspectral cameras systems can be also used. Cameras can provide video frame data at a rate ranging from 1 frames per second to as much as 240 frames per second. In one embodiment, the display is configured to display a real time video and audio feed to the user. In other embodiments, cameras can be used for biometric purposes, including detecting heart or breathing rates, determining body temperature, or monitoring other bodily functions.

In other embodiments, user position or distance measurements to a user can be made, alone or in combination, with a scanning lidar system, an imaging lidar system, a radar system, a monocular system with supported distance determination, and an ultrasonic sensing system. The lidar system can include multiple scanning lasers and suitable time-of-flight measurement systems to provide relative or absolute distance and instantaneous user position information.

In some configurations, the exercise machine display 102 is capable of combining virtual and augmented reality methods with real-time video and/or audio and with real-time user position or force data. This permits, for example, providing three dimensional (3D) augmented reality with dynamics virtual pointers, text, or other indicators to allow a user to better interact with the exercise machine or connected friends or exercise class members, while still providing real-time information such as instantaneous or average force applied for each exercise, heart rate, or breathing/respiratory rate.

As will be understood, interactive exercise machine system 100 can include connections to either a wired or wireless connect subsystem for interaction with devices such as servers, desktop computers, laptops, tablets, smart phones, or sensor equipped exercise equipment. Data and control signals can be received, generated, or transported between varieties of external data sources, including wireless networks, personal area networks, cellular networks, the Internet, or cloud mediated data sources. In addition, sources of local data (e.g. a hard drive, solid state drive, flash memory, or any other suitable memory, including dynamic memory, such as SRAM or DRAM) that can allow for local data storage of user-specified preferences or protocols. In one particular embodiment, multiple communication systems can be provided. For example, a direct Wi-Fi connection (802.11b/g/n) can be used as well as a separate 4G cellular connection.

Figure 2A:
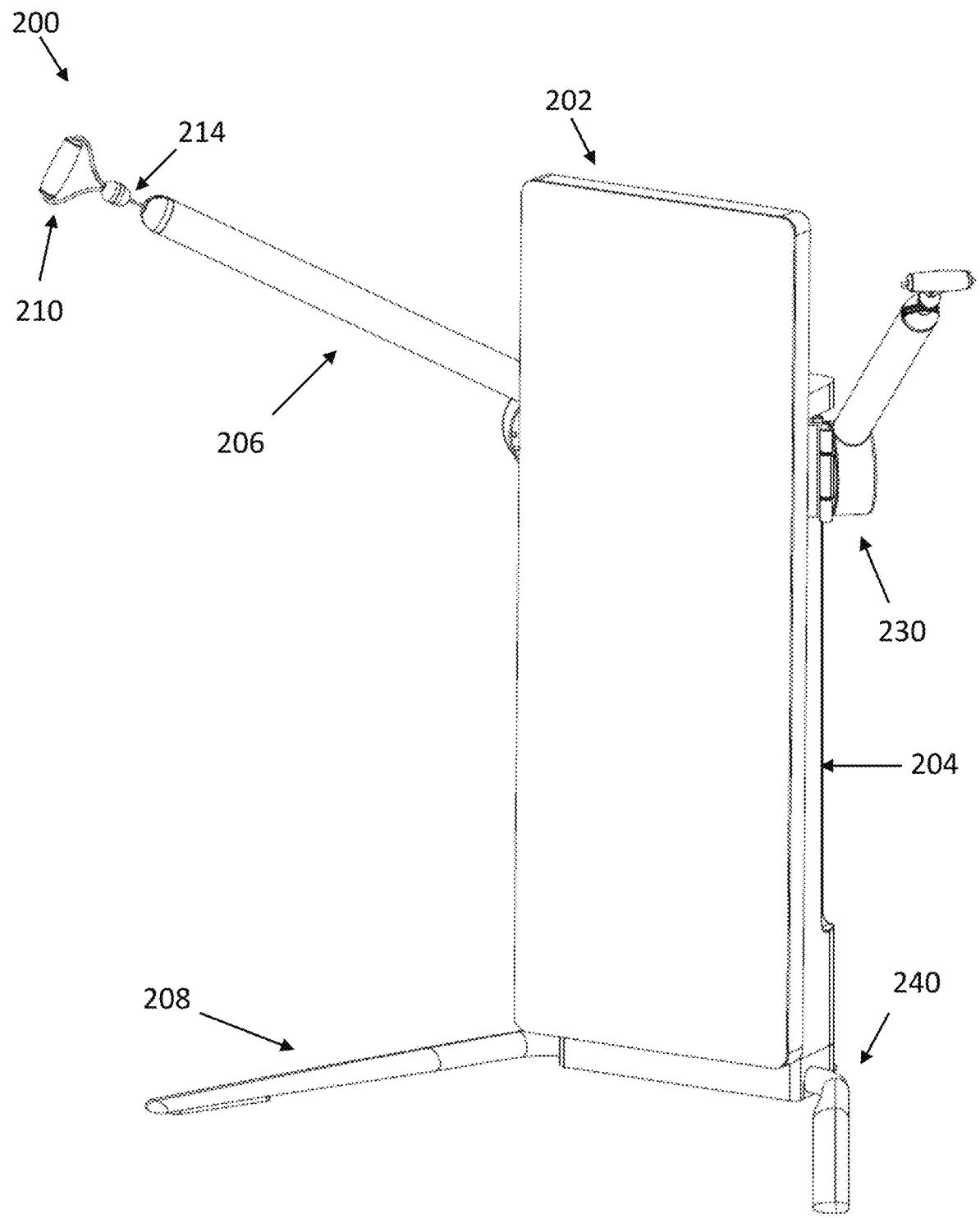
FIGS. 2A-G illustrate various extended arm and folded views of an interactive exercise machine with legs.
Figure 2B:
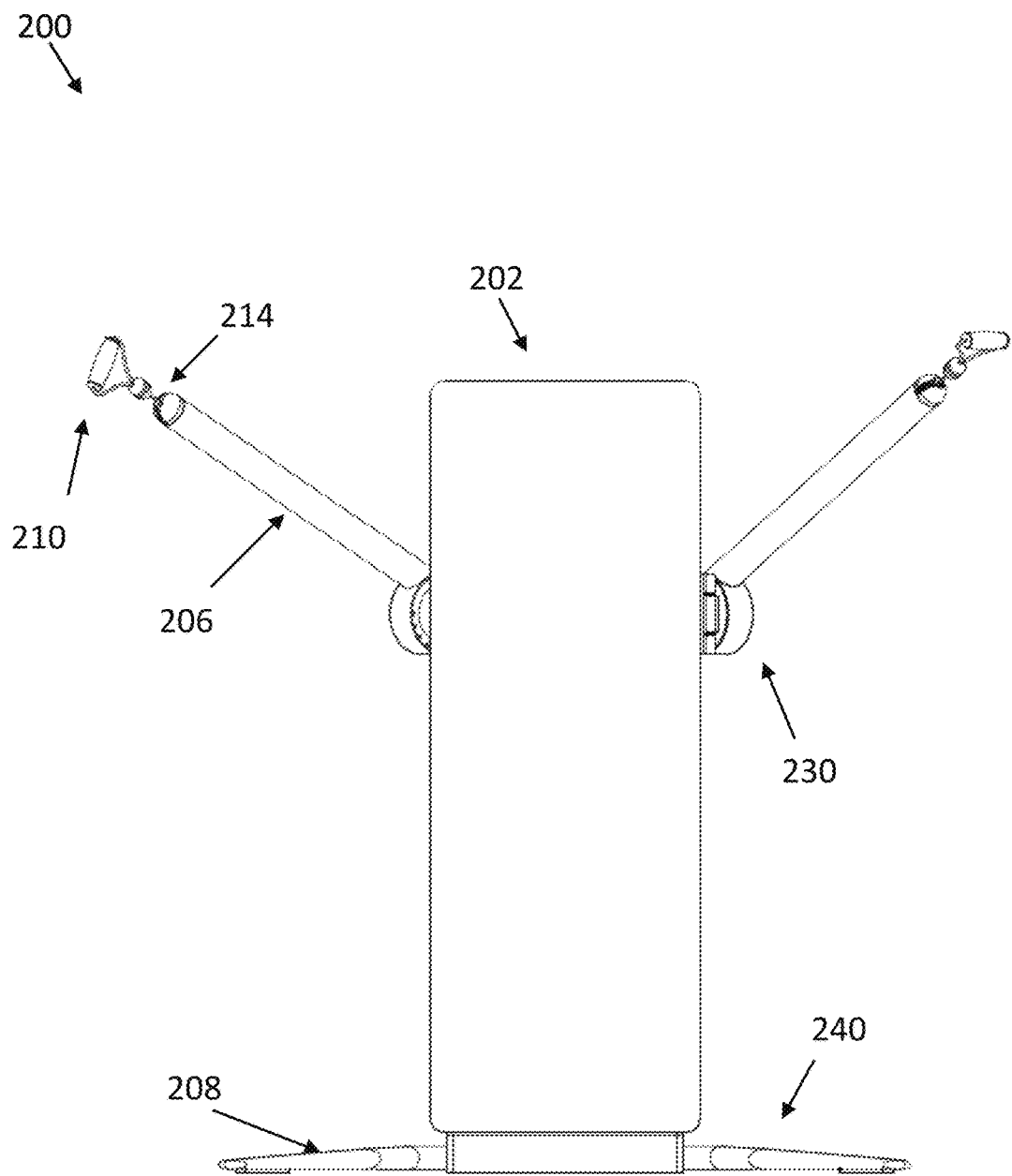
Figure 2C:
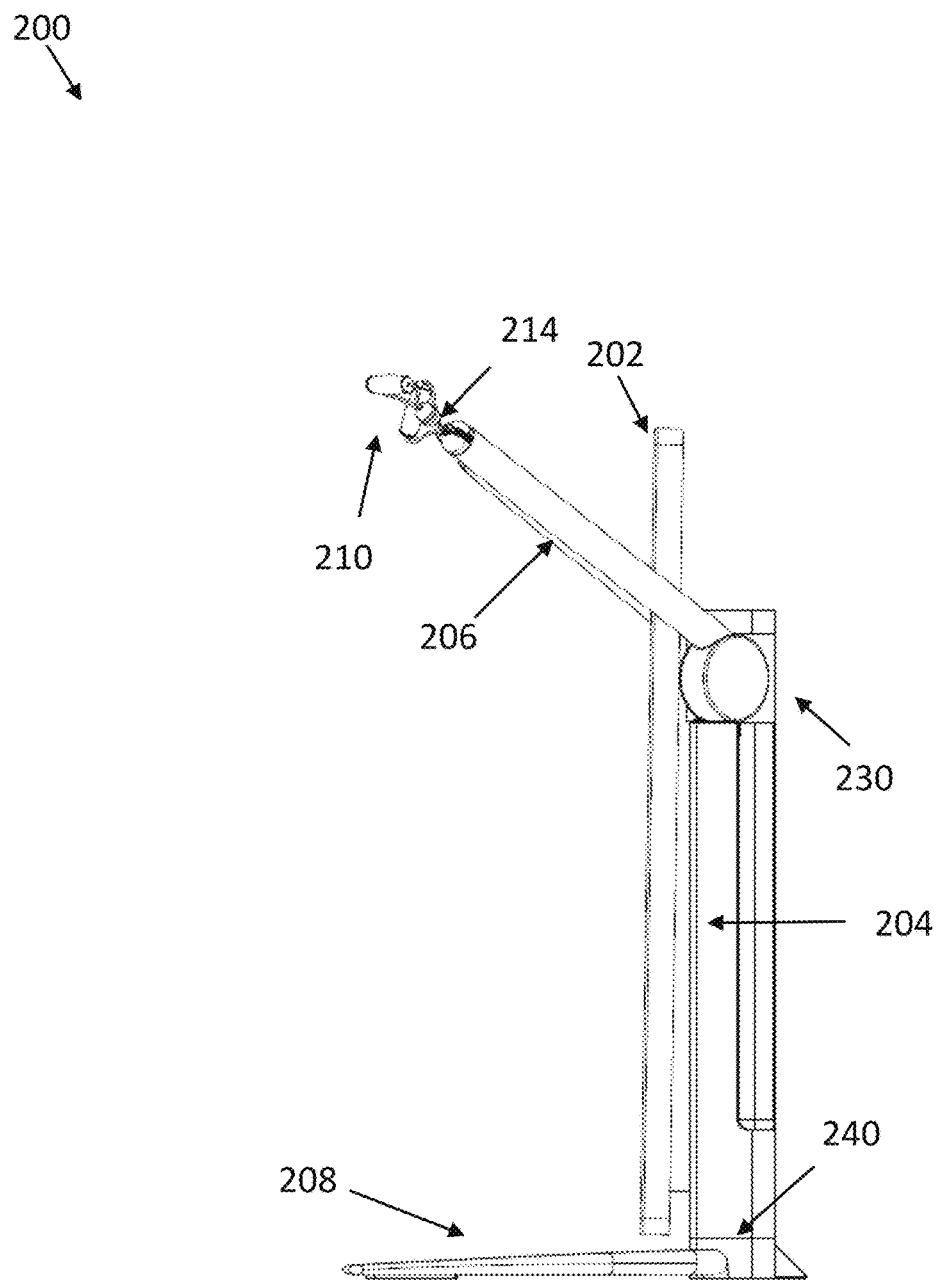
Figure 2D:
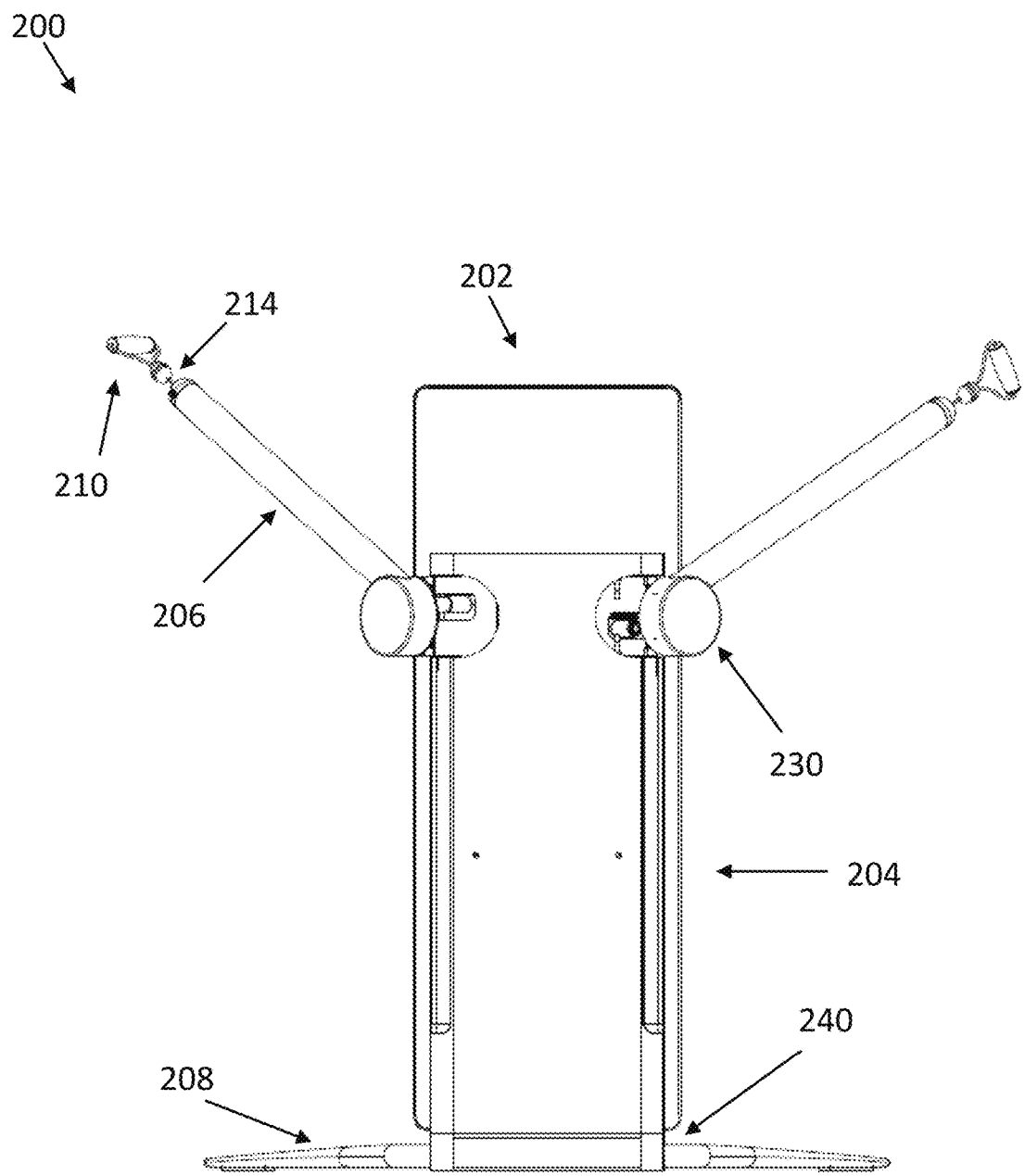
Figure 2E:
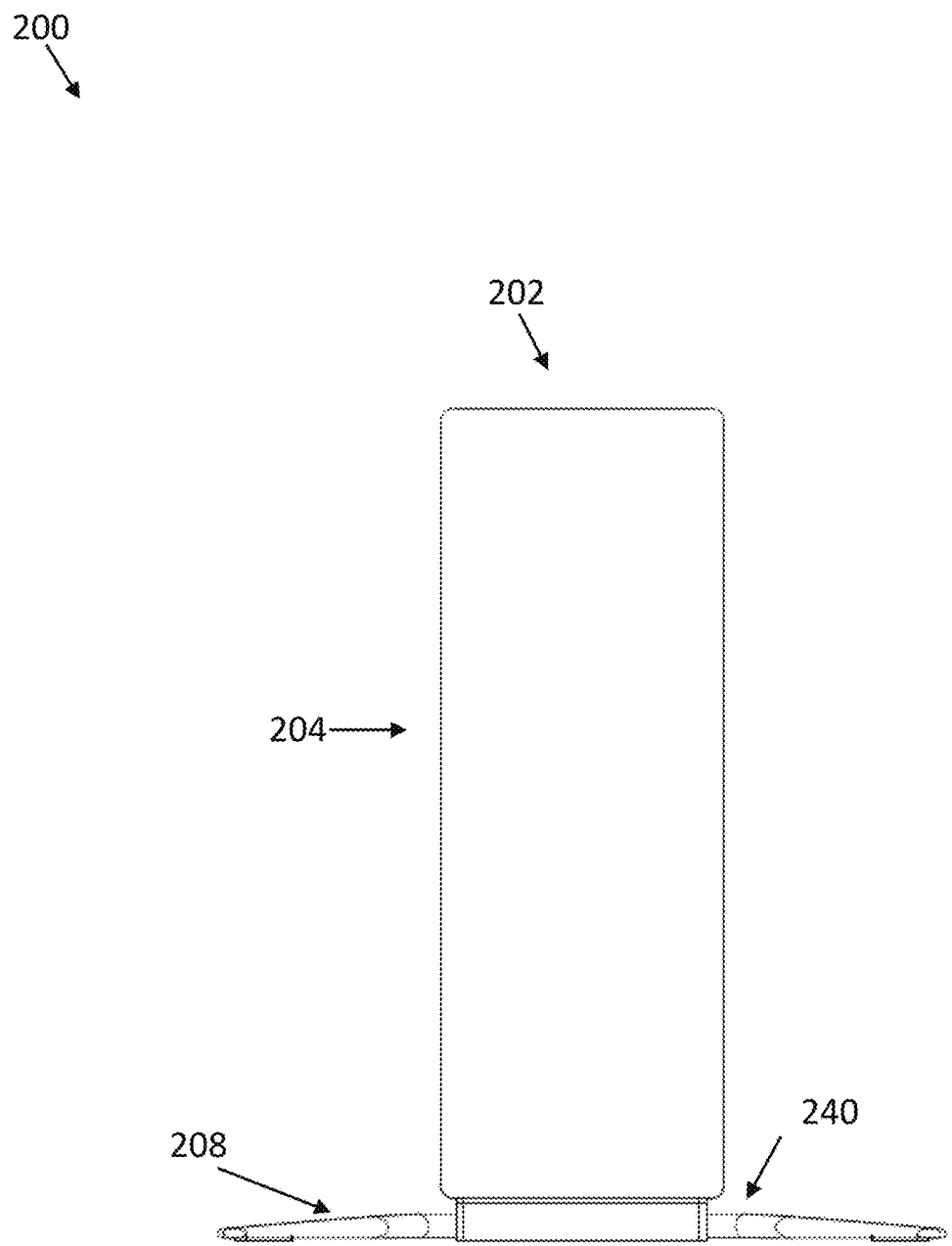
Figure 2F:
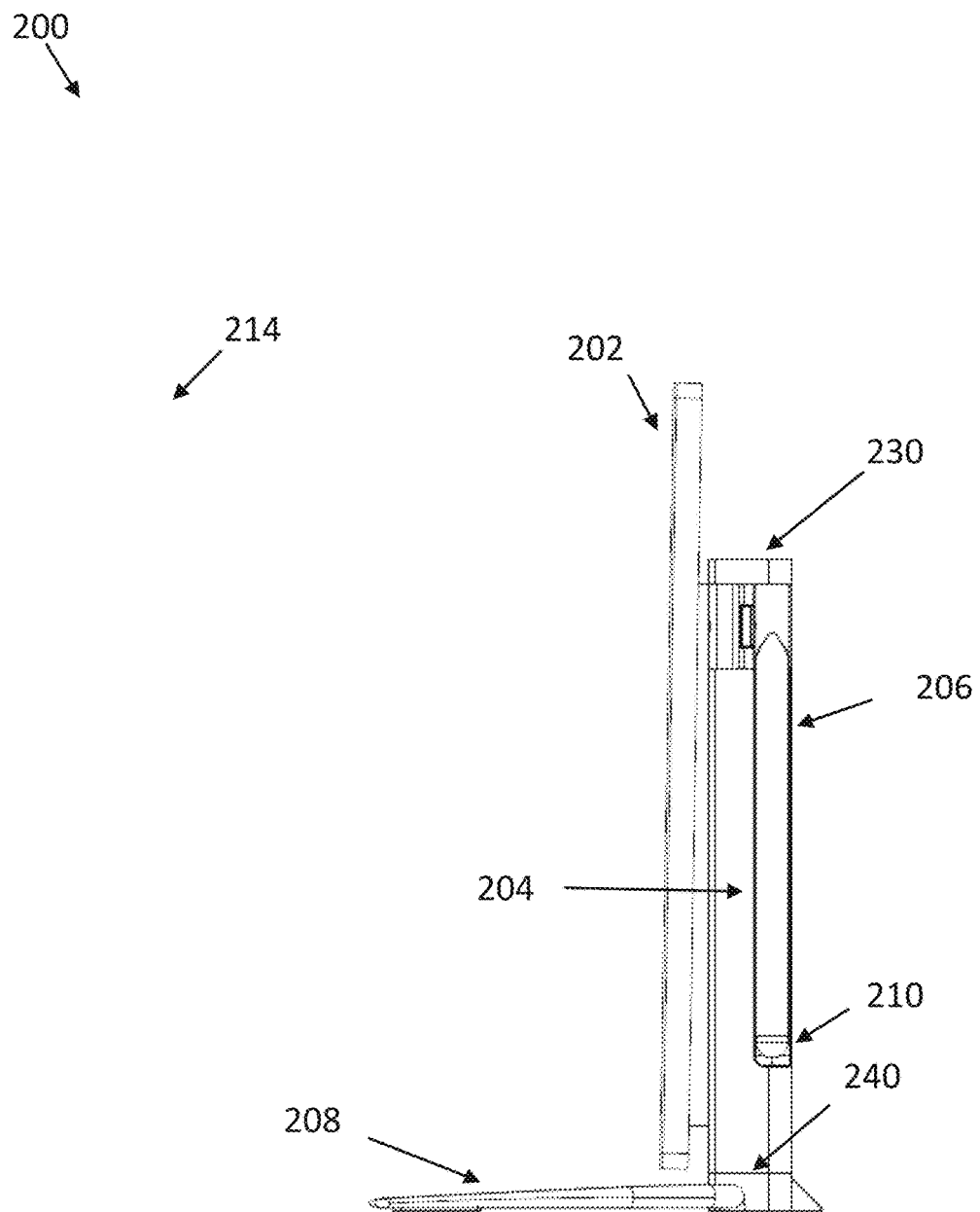
Figure 2G:
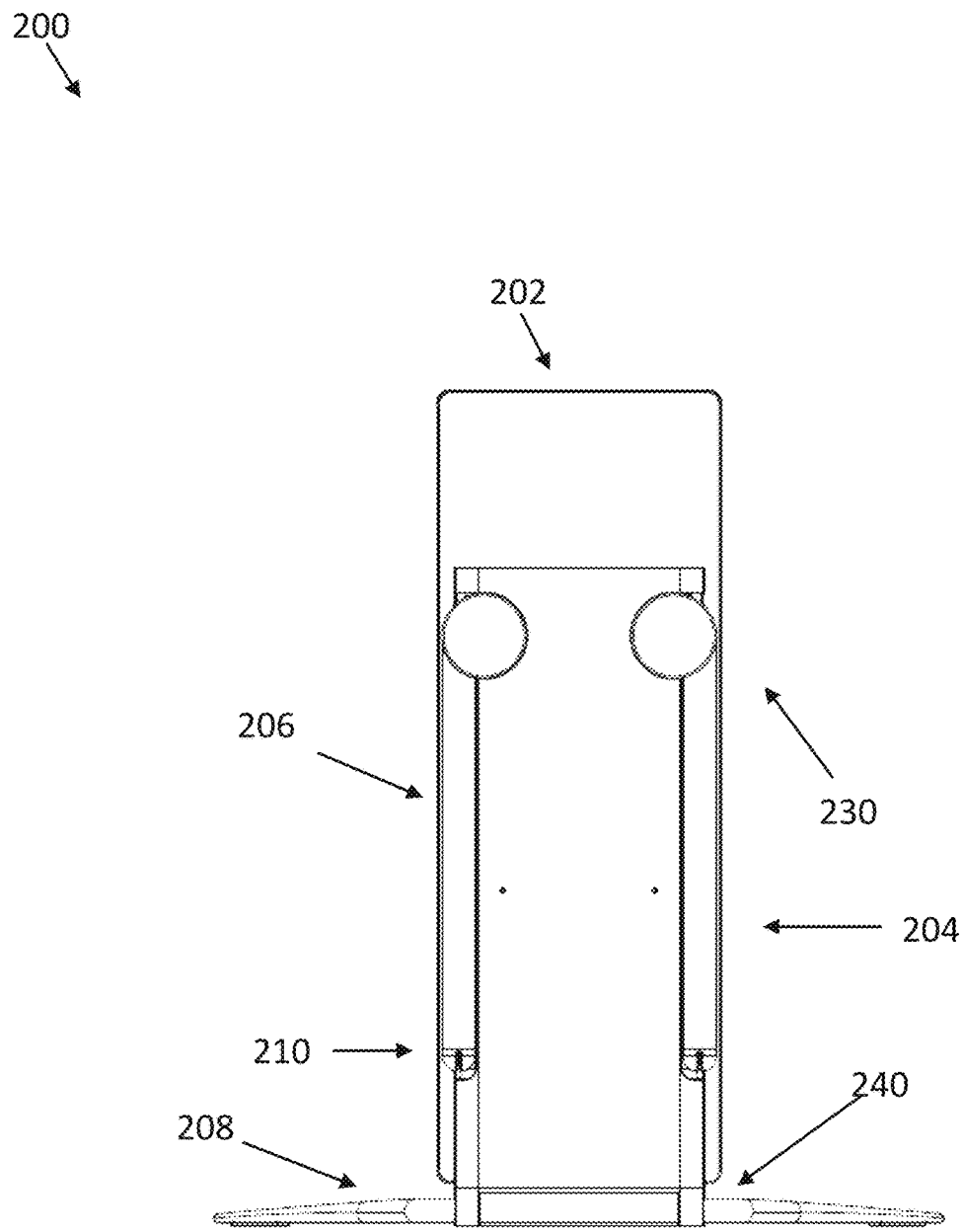

FIGS. 2A-H illustrate various views of multiple interactive exercise machine embodiments. FIG. 2A shows an interactive exercise machine 200 in perspective, with arms and legs extended. FIG. 2B shows an interactive exercise machine 200 in front view, with arms and legs extended. FIG. 2C shows an interactive exercise machine 200 in side view, with arms and legs extended. FIG. 2D shows an interactive exercise machine 200 in rear view, with arms and legs extended. FIG. 2E shows an interactive exercise machine 200 in front view, with arms folded and legs extended. FIG. 2F shows an interactive exercise machine 200 in side view, with arms folded and legs extended. FIG. 2G shows an interactive exercise machine 200 in rear view, with arms folded and legs extended.

Similar to that described with respect to FIG. 1, the interactive exercise machine 200 includes an exercise machine display 202 held by a mechanical support system 204. The display 202 can be at least partially covered with a semi-reflective coating or mirror that reflects an image of a user (not shown), while still allowing viewing of videos or information presented by the display 202.

The mechanical support system 204 is supported by legs 208 attached via a leg hinge assembly 240 that allows fixed attachment or folding of the legs for easy storage. Movable arms 206 are attached to the mechanical support system 204. Graspable handles 210 are connected to force sensor 214 monitored cords extending through the movable arms 206. The arms 206 are attached to a multi-axis arm hinge assembly 230 that permits pivoting, vertical plane rotation of the arms 206, as well lateral rotation about a hinge attached to the mechanical support system 204. The arms 206 can be independently positioned and locked into place. This arrangement allows for providing a wide variety of actively adjustable, force sensor monitored, variable resistant force exercises to a user.

Figure 2H:
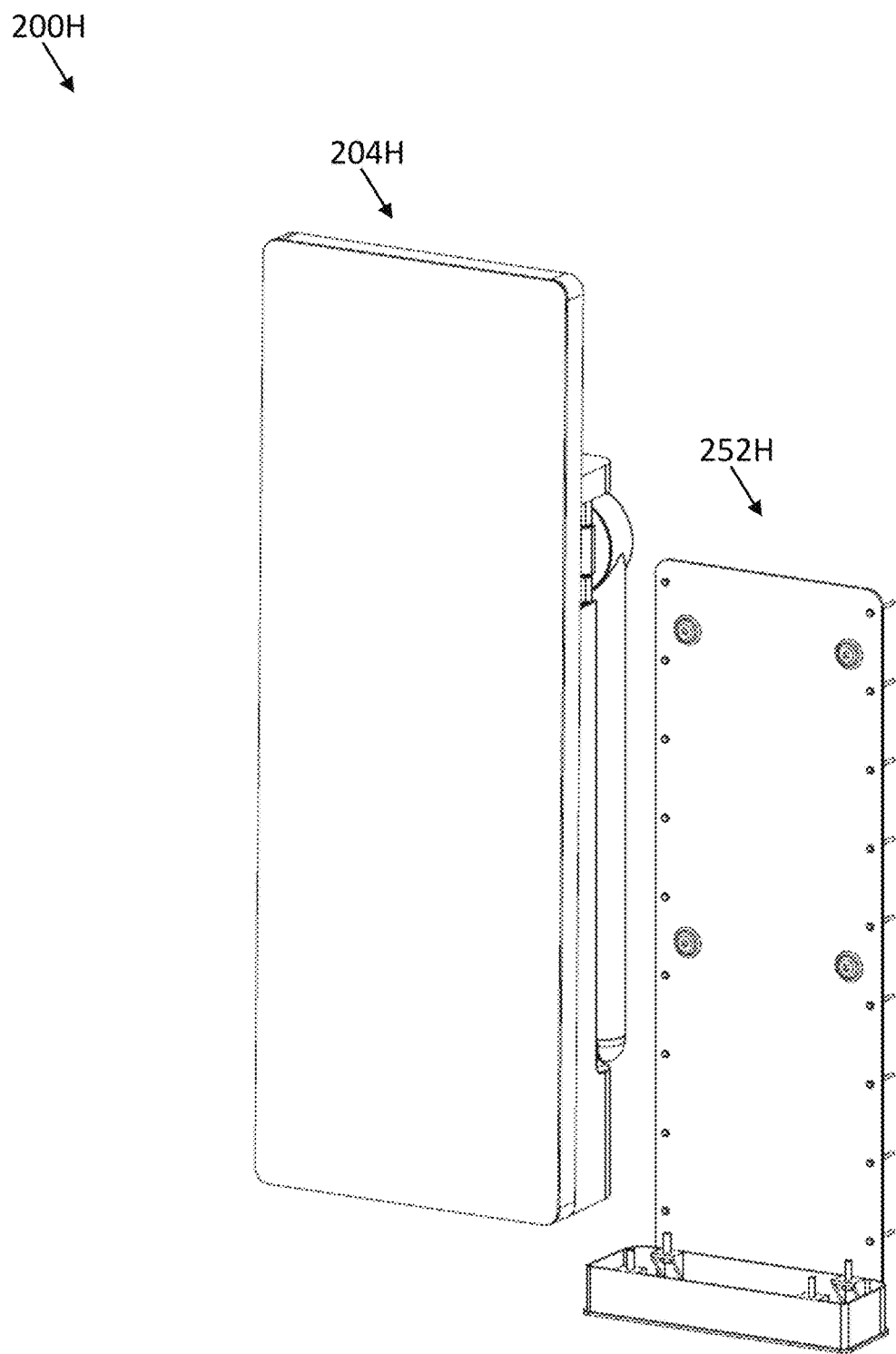
FIG. 2H illustrates a wall mounted interactive exercise machine.
Figure 21:
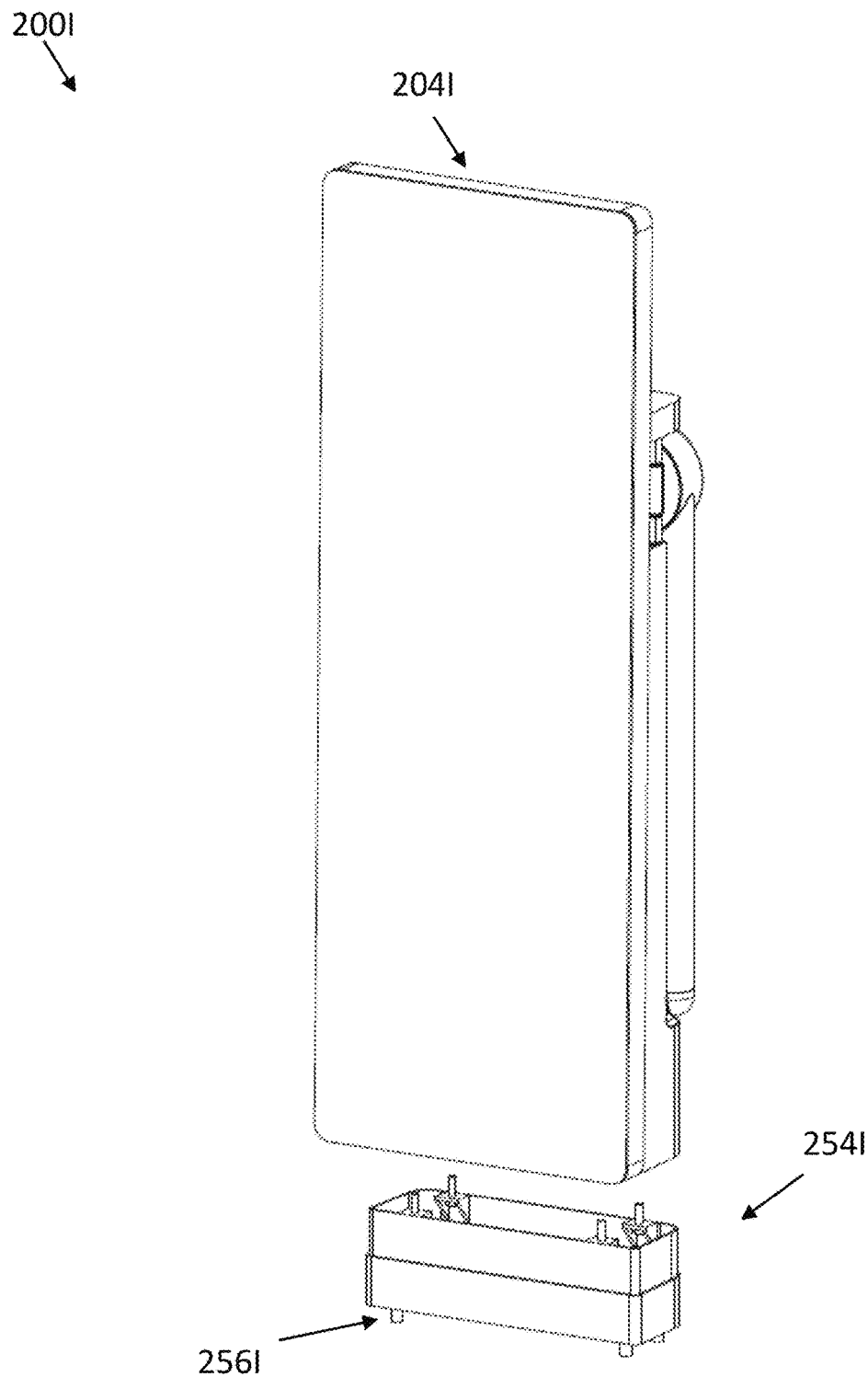

FIG. 2H shows an alternative embodiment of interactive exercise machine 200H with mechanical support system 204H in perspective view, with arms folded, legs omitted, and configured for wall mounting using a wall support unit 252H. The wall support unit 252H can be temporarily or permanently bolted to a wall (not shown). The mechanical support system 204H can be locked, bolted, or otherwise attached to the wall support unit 252H.

FIG. 2I shows an alternative embodiment of interactive exercise machine 200I in perspective view, with arms folded, legs omitted, and configured for floor mounting using bolt attachment. The floor mounting unit 254I can be temporarily or permanently bolted to a floor using bolts 256I. The mechanical support system 204I can be locked, bolted, or otherwise attached to the floor mounting unit 254I.

Figure 3A:
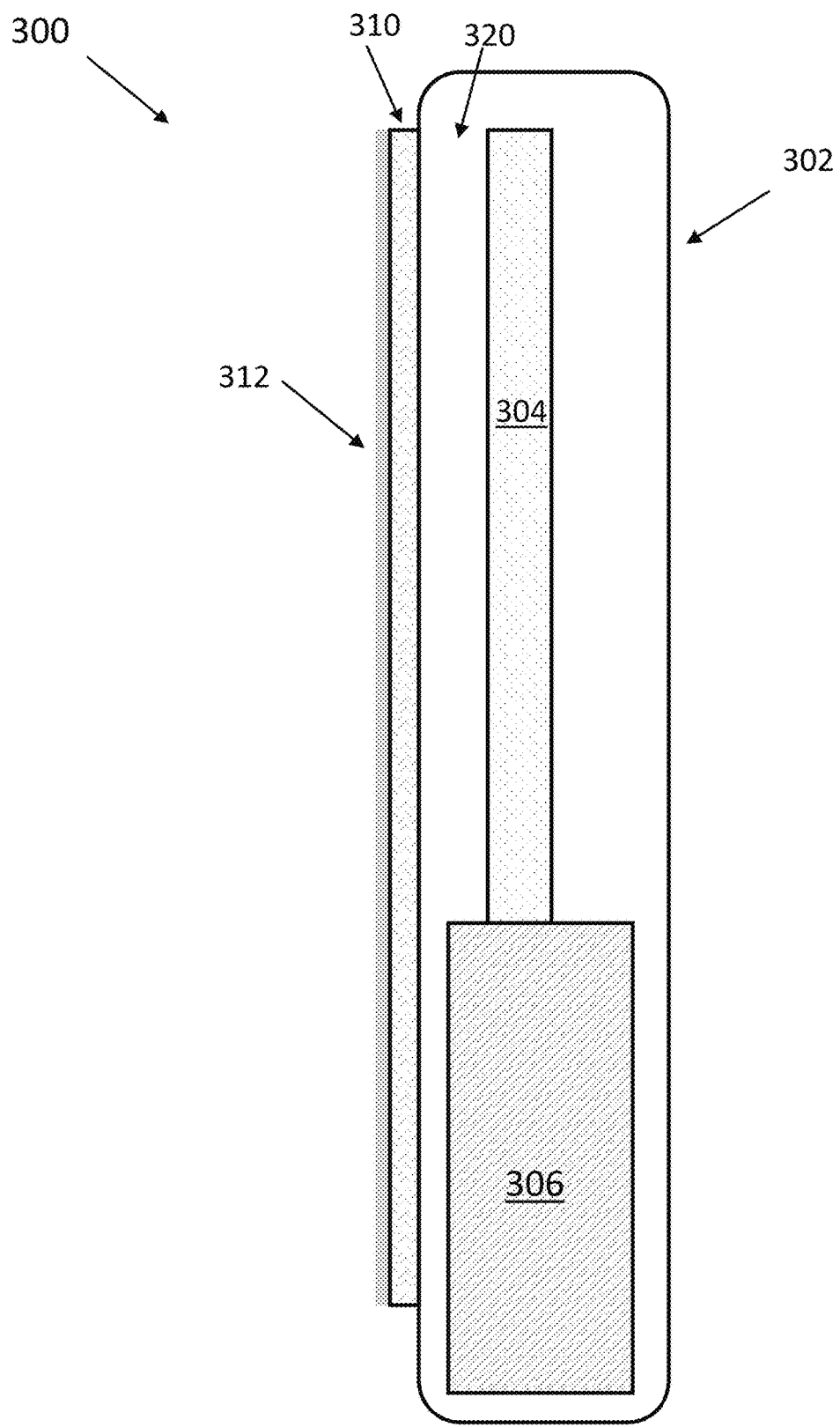
FIG. 3A illustrates in cross section mirror and touch screen positioning with respect to a display.

FIG. 3 illustrates in cross section mirror and touch screen positioning with respect to a display (not to scale). A seen in FIG. 3 a housing 302 surrounds a display 304 and an electronics module 306 that controls operation of the display 304. Also shown are a touchscreen 310 having a partially silvered mirror 312 attached, with the combination being mounted to housing 302 with a small included air gap 320. In some embodiments the air gap 320 is filled with an optically transparent adhesive that directly attaches the touch screen to the display 304. In other embodiments, the touchscreen can be entirely omitted, and the mirror 310 can be formed as a coating on the display 304 or separated provided on a glass or other substrate. In FIG. 3, the display 304 is shown as extending from near the top of the housing 302 partially downwards to the floor. In other embodiments, the display can fully extend to the floor. In still other embodiment, the display does not extend to the top of the housing 302 but ends several centimeters away from the housing top. Similarly, the mirror 310 can be coextensive with the display, cover a portion near the top of the display, near the bottom of the display, or in between the top and bottom of the display. In some embodiments, tiled or multiple displays can be used.

Figure 4A:
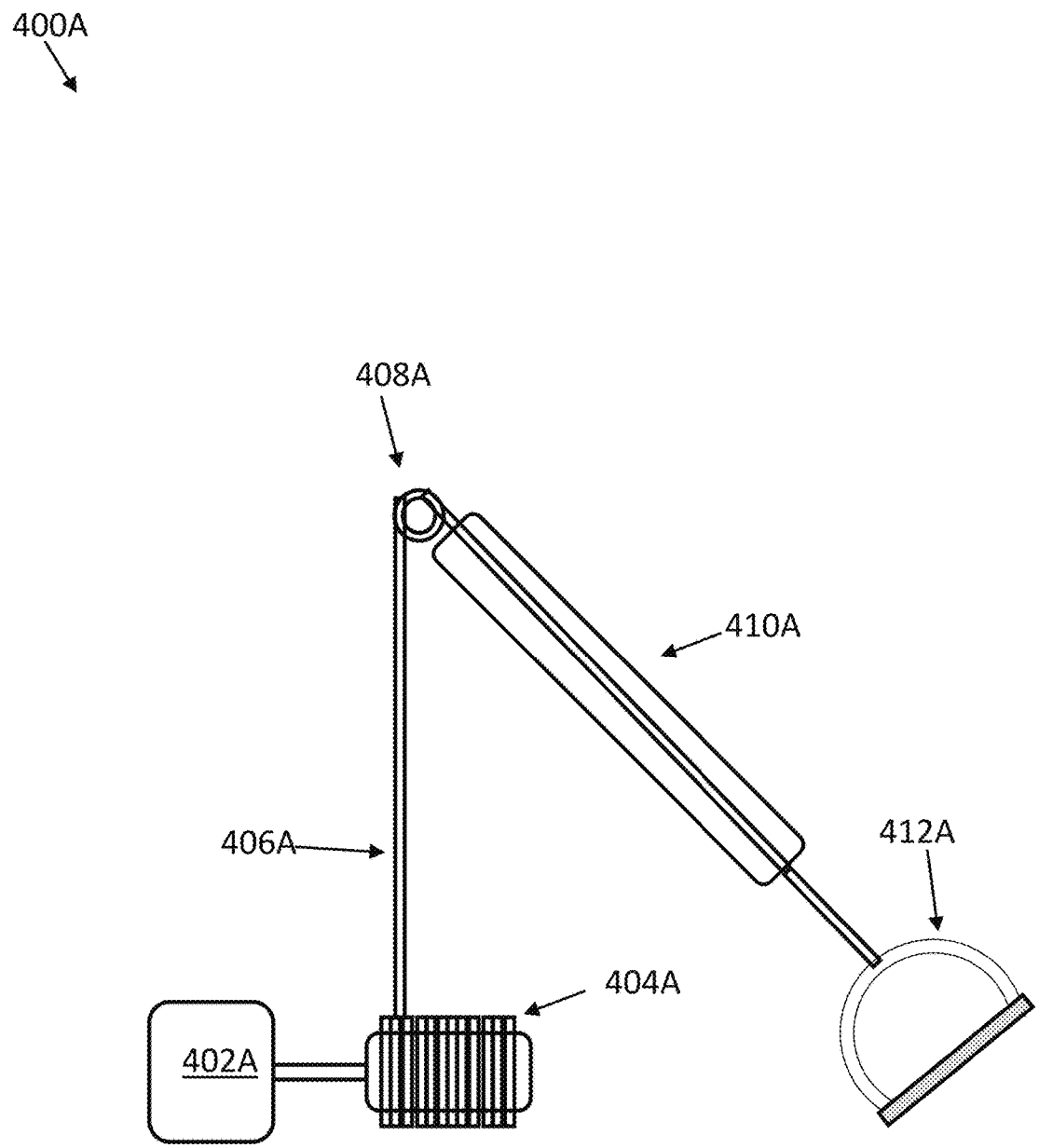
FIGS. 4A-E illustrate force resistant reel assemblies and component parts.

FIG. 4A illustrates a force resistant reel assembly 400A that can be adapted for use in an interactive exercise machine system 100 or 200 such as discussed with respect to FIGS. 1 and 2A-I. The force resistant reel assembly can include a motor 402A connected to a reel 404A for winding a cord 406A. Redirection of the cord and force sensing is provided by a sensor/pulley assembly 408A. The cord can be surrounded and protected by a movable arm 410A and attached to graspable handle 412A. The sensor/pulley assembly 408A provides redirect at a 1:1 mechanical advantage, but multiple pulleys can be used to provide greater or lesser mechanical advantage, or additional cord redirection if needed.

In operation, the sensor/pulley assembly 408A provides instantaneous force data to allow for immediate control of applied force by motor 402A. Applied force can be continuously varied, or in certain embodiments applied stepwise. In some embodiments, if the degree of applied user force is great enough to cause potential movement or tip-over of an interactive exercise machine system 100 or 200, the motor 402A and reel 404A can allow the cord to run free, lowering the possibility of tip-over. In some embodiments, optional cord braking systems, tensioners, or sensors can be used. Force, cord distance, acceleration, torque or twist sensors can also be used in various embodiments. Advantageously, force control can be modified using scripted control inputs or dynamic force adjustments based on three-dimensional user position and/or kinematic user motion models. This allows for fine control of force applied during complex exercise routines, for improved training or high intensity weightlifting.

Figure 4B:
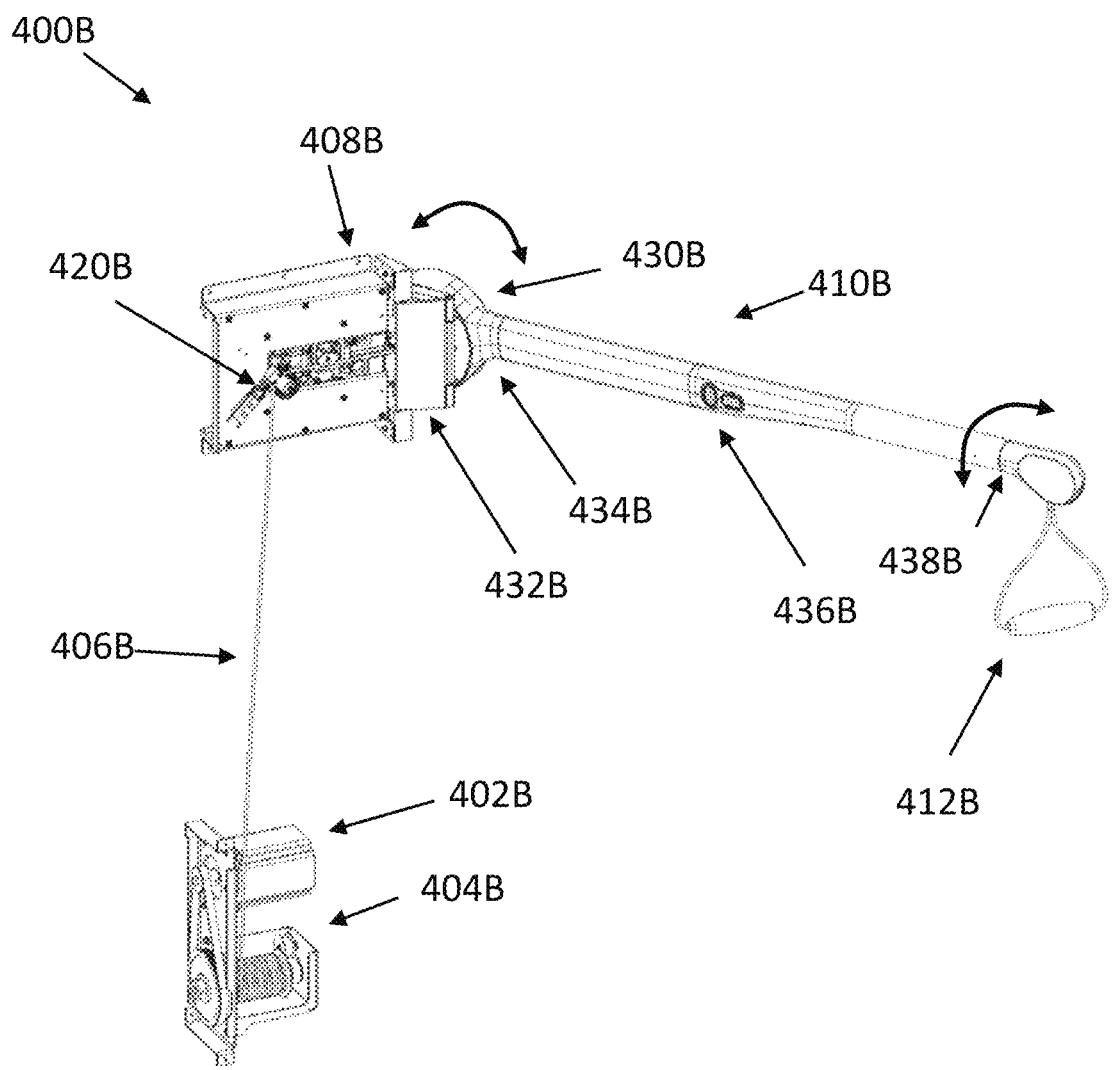

FIG. 4B illustrates in more detail a force resistant reel assembly 400B such as described with respect to FIG. 4A. The force resistant reel assembly can include a force controllable motor 402B that is belt drive connected to a reel 404B for winding/unwinding a cord 406B. In some embodiments a V-groove belt, multi-v-groove belt, or other techniques can be used to reduce or eliminate mechanical cogging or variation in applied force. Redirection of the cord and force sensing is provided by a sensor/pulley assembly 408B that includes a force sensor 420B. The cord 406B can be surrounded and protected by a movable arm 410B and attached to graspable handle 412B. Various features allow for adjustment of arm position, including multi-axis arm hinge assembly 430B with a hinge plate mechanism 432B and a rotational arm mechanism 434B for pivoting upward and downward arm rotation. Arm length can be adjusted by use of an articulating arm system with position change buttons 436B. A rotating arm terminus 438B allows for free rotation of the arm end.

Figure 4C:
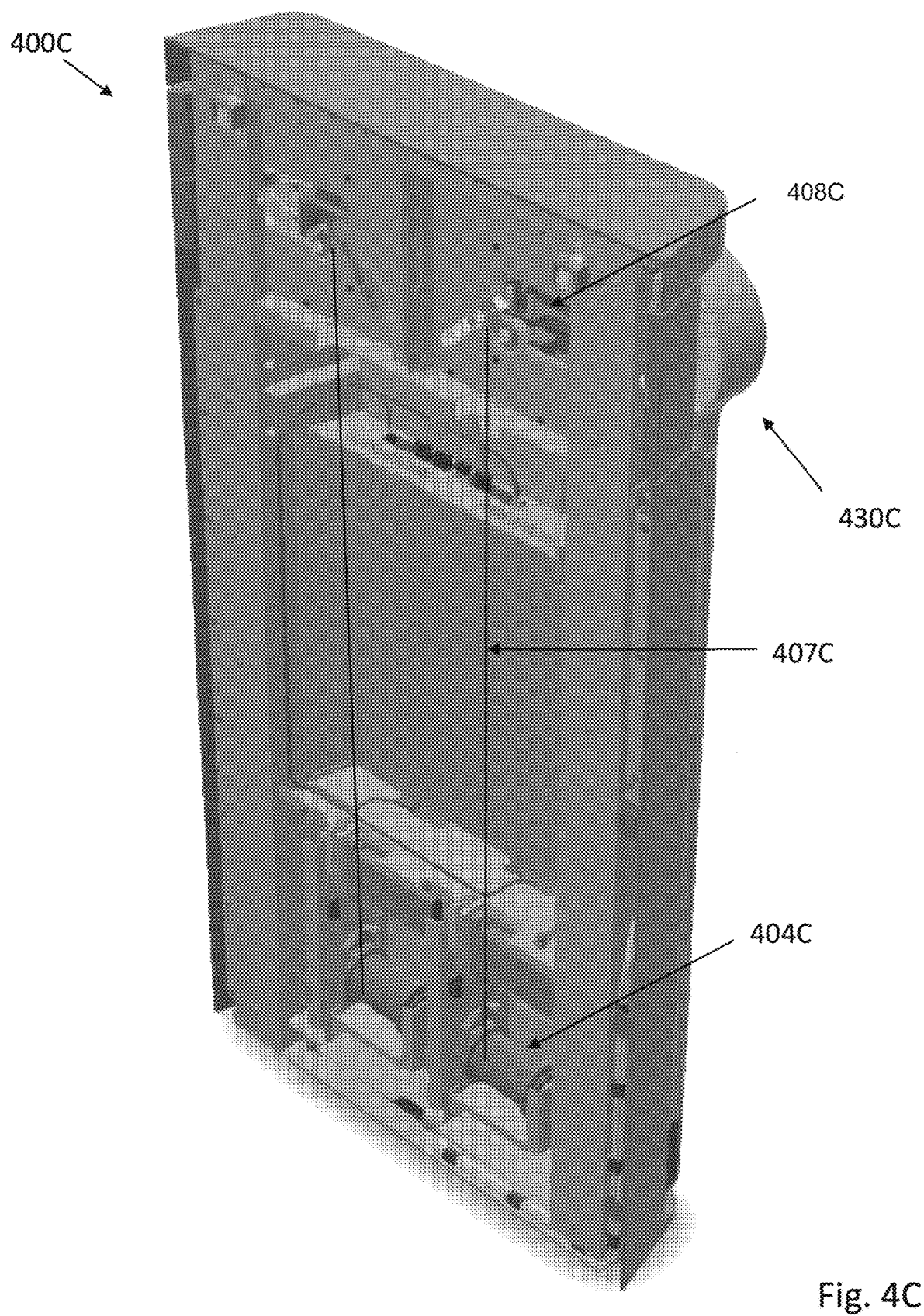

FIG. 4C illustrates a backside of an exercise machine 400C showing in more detail mounting of a pair of force resistant reel assemblies 404C similar to those described with respect to FIGS. 4A and 4B. The force resistant reel assemblies are located near the base of the exercise machine 400C. Redirection of a cord 407C and force sensing is provided by a sensor/pulley assembly 408C. In one embodiment, multiple or redundant force sensors can be used to reduce instances of operational failure or provide higher accuracy force sensing. Further redirection of the cord is provided using multi-axis arm hinge assembly 430C connected to a movable arm with graspable handle (not shown).

Figure 4D:
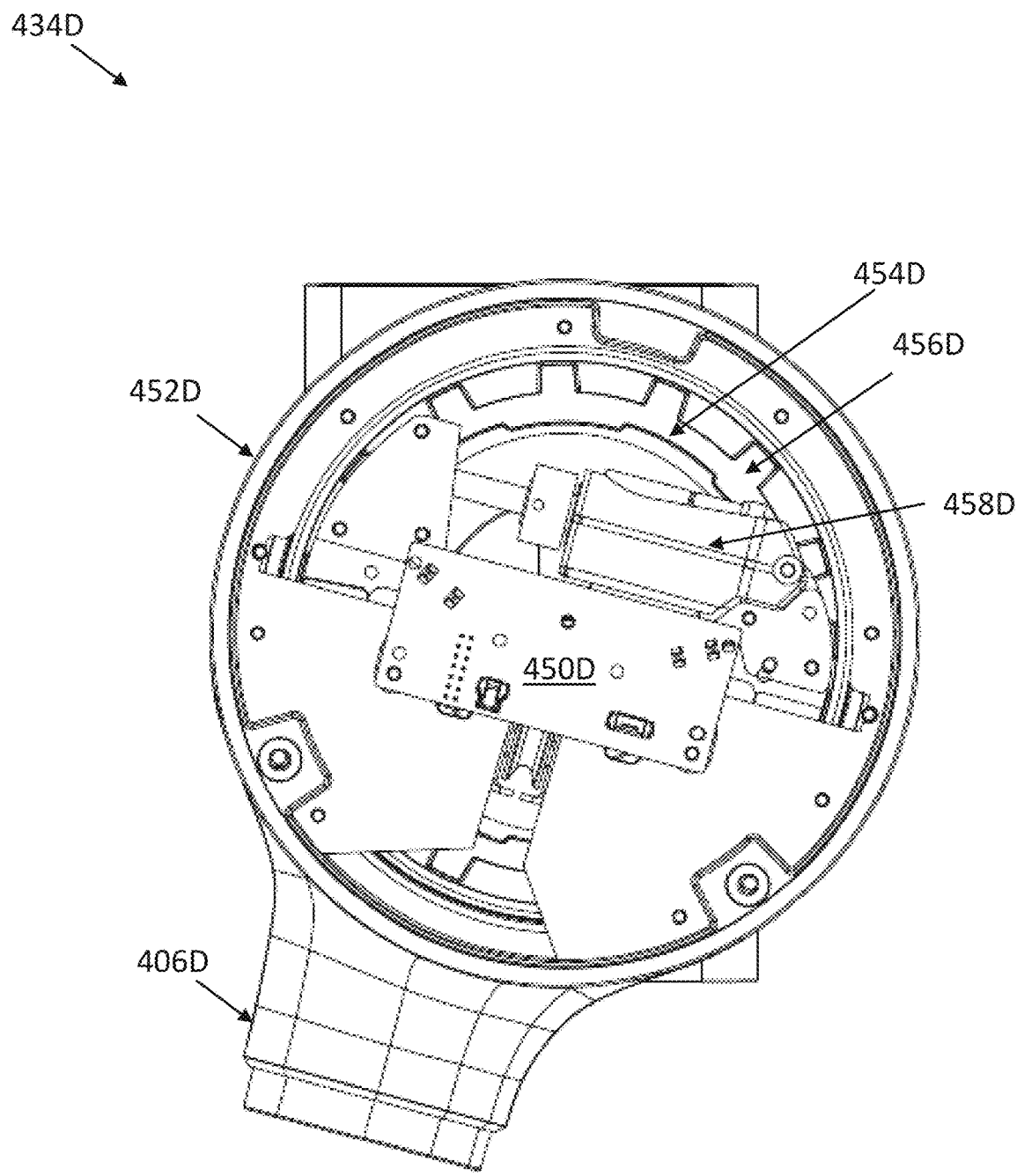

FIG. 4D illustrates in more detail a rotational arm mechanism 434D similar to that described with respect to FIG. 4B. The rotational arm mechanism 434D includes a rotating arm base 452D attachable to a fixed inner ring plate 454D having multiple positioning teeth 456D. A motor driven release mechanism 458D controlled by a height control electronic board 450D is capable of rotating and locking an arm 406D into a desired position. Optionally, a manually actuated release mechanism can be used.

Figure 4E:
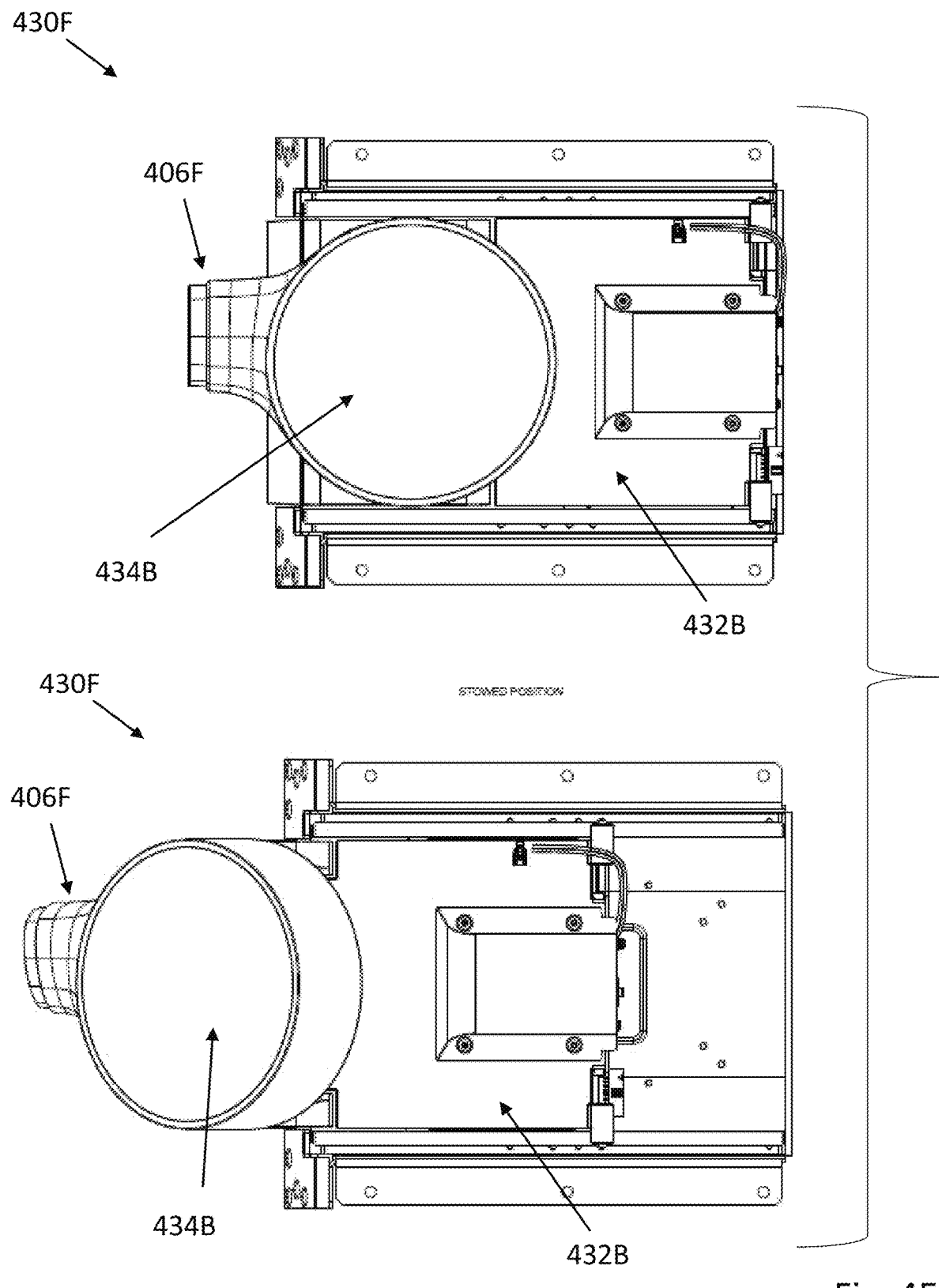

FIG. 4E illustrates in more detail a multi-axis arm hinge assembly 430F similar to that described with respect to FIGS. 4B and 4D. A stowed position view and an example position 1 are indicated. As can be seen, the rotational arm mechanism 434B is slidably attached to the hinge plate mechanism 432B. When in a stowed position with the display inactivated, the arms are not readily visible from a front of the interactive exercise machine and the mirrored front appears to be a conventional mirror.

Figure 5:
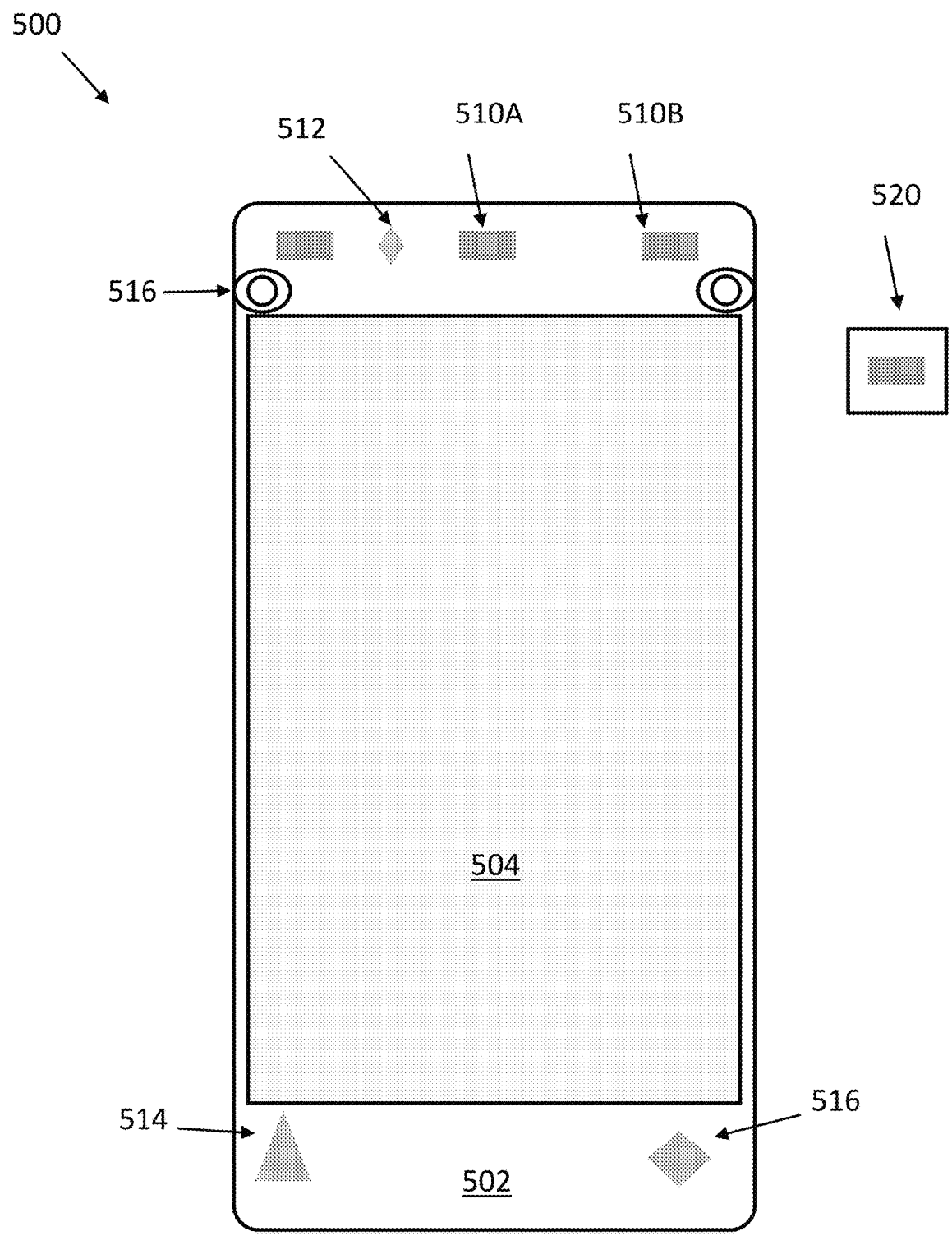
FIG. 5 illustrates positioning of various sensor systems on the interactive exercise machine.

FIG. 5 illustrates positioning of various sensor systems on the interactive exercise machine system 500. An exercise machine 502 includes on-board sensors and can be connected (wired or wireless) to remote sensors. Sensors can include, but are not limited to, center mounted three-dimensional camera 510A, side mounted three-dimensional camera 510B, acoustic sensors such as microphone 512, an environmental condition monitor 514 (which can include humidity, temperature, ambient light, etc.), and force or position sensors 516 (which can include one-, two-, or three-axis accelerometers, gyroscopes, or GPS/GNSS systems). The display 504 can be touch or pressure sensitive. Remote cameras 520 can be used, and the system can also support speakers 516 for audio instructions or feedback.

Figure 6A:
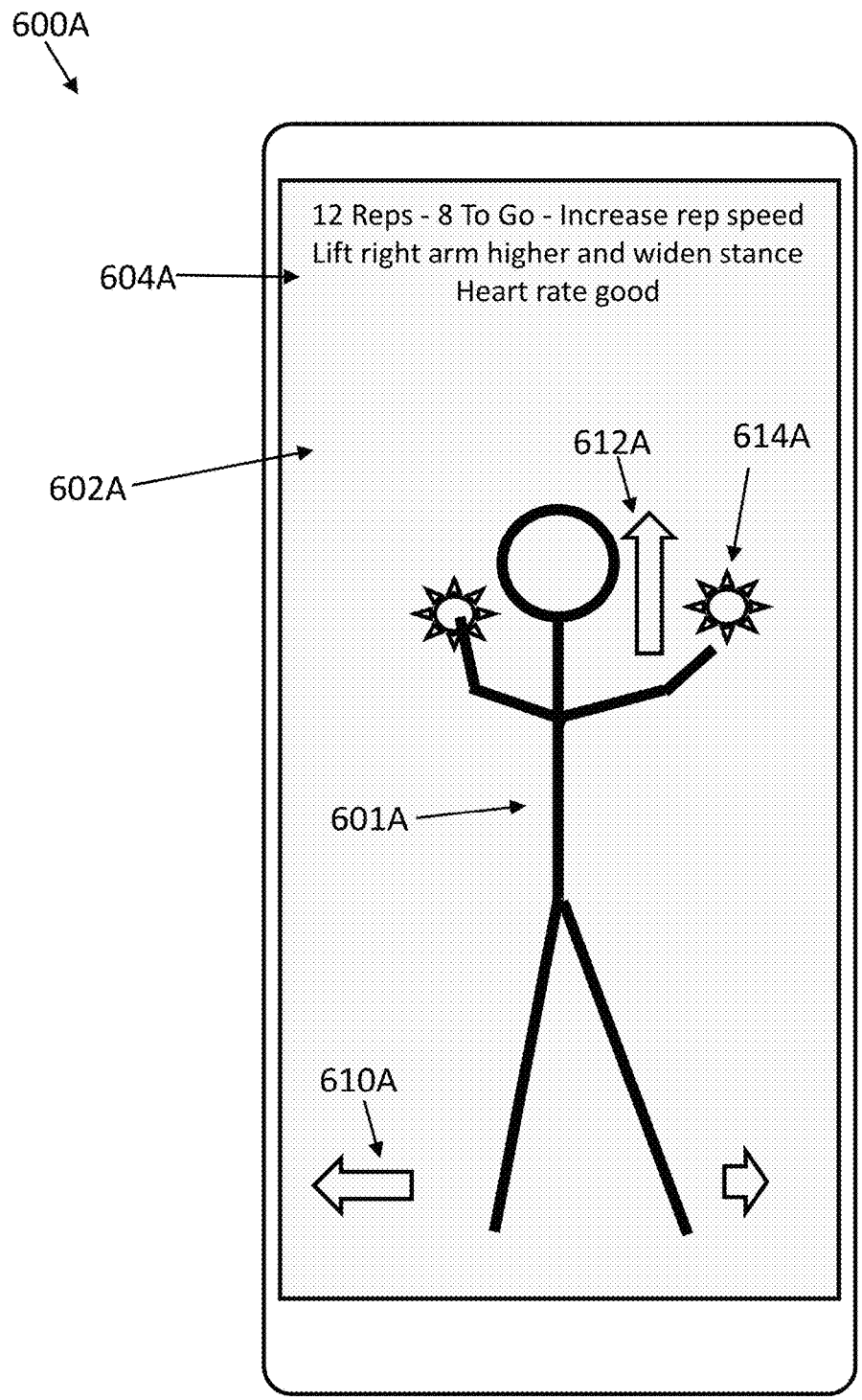
FIGS. 6A-B illustrates floating views with an augmented reality overlay.

FIG. 6A illustrates an exercise machine system showing a floating view 600A with an augmented reality overlay 602A. A user 601A (stick figure) can have their image reflected by a partially silvered mirror covering the display such as previously discussed with respect to FIGS. 1 and 3. The backing display can provide continuously updated textual, graphical, or video information that is positioned on the screen based at least in part on user position. For example, textual information 604A can be placed above the user's image. In some embodiments, target positions 614A for arm/hand position can be illustrated, and arrows 612A direct the user to adopt a proper exercise position. Similarly arrows 610A can indicate to a user the need to widen stance, which can also be textually indicated, provided by audio directions, and/or provided by video directions. In some embodiments, audio instructions can be provided. In other embodiments wirelessly connected haptic signaling devices can be used, with vibration frequency or haptic intensity used to provide user feedback.

Figure 6B:
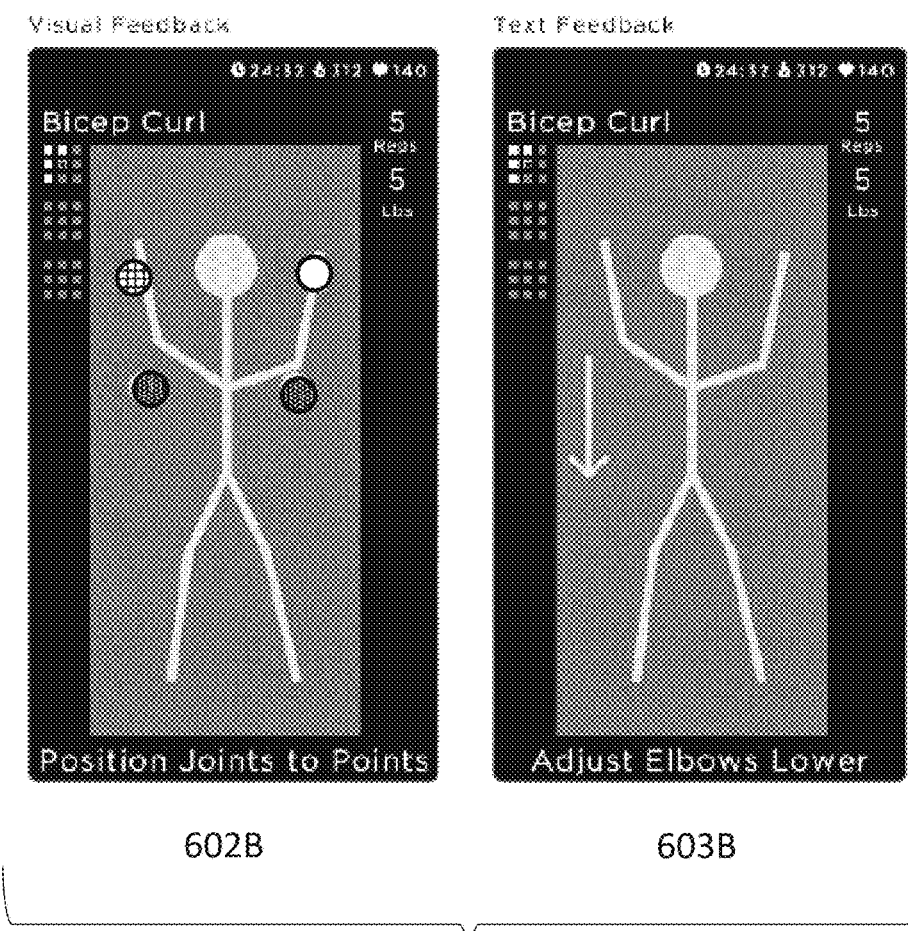

FIG. 6B illustrates displays 600B for an exercise machine system. Shown are a floating view with two alternative screen displays 602B and 603C of an augmented reality overlay. A cartoon rendering, stick figure, or rudimentary skeletal representation of a user can be displayed. Screen display 602B provides primarily visual feedback, with target positions for hands, wrist, elbows, or other bodily features being indicated. In screen display 602B, correct positioning of a hand or other body part is indicated by a light colored circle, while darker circles indicate incorrect positioning. This provides visual feedback to a user, who can move until light colored circles shown for the indicated body parts. Alternatively, as indicated with screen display 603B, text can be used to direct a user to, for example, adjust elbows to a lower position. Similarly, directional arrows can indicate to a user the need to lower elbows. As will be appreciated, other graphic elements than circles can be used, including but not limited to other graphic indicia, highlight, or bright or dark regions. In some embodiments graphic elements can include a graphical overlay on a reflection of a user, graphic overlay on video of user, animations, or graphical overlays on trainer video. Both static or motion graphics can be used. Visual feedback may also include additional windowed video clips, inserted video clips into trainer video showing a trainer providing specific feedback, and audio overlays or instructions.

Figure 7:
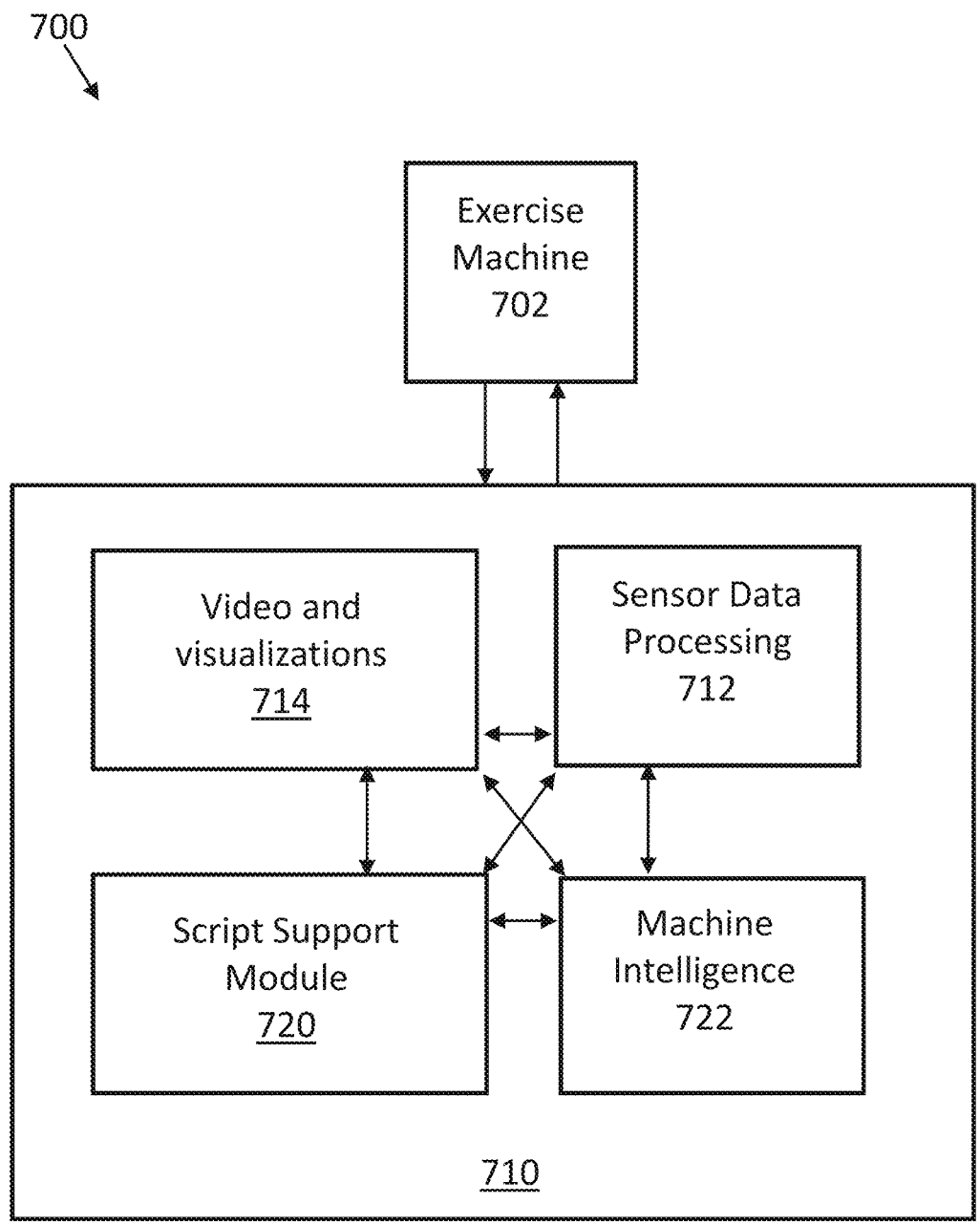
FIG. 7 illustrates data handling and analytics for the interactive exercise machine.

FIG. 7 illustrates data handling and analytics for the interactive exercise machine system 700. An exercise machine 702 can be supported by a range of data processing functions 710. These can include sensor data processing 712, video and visualizations playback and creation 714, script support module 720 for providing fixed or dynamically modifiable exercise scripts to support force profiles of exercises or exercise routines, and machine intelligence to support kinematic modelling/visualization and improve exercise efficacy using immediate user data, historical user data, and group or other social data.

Figure 8:
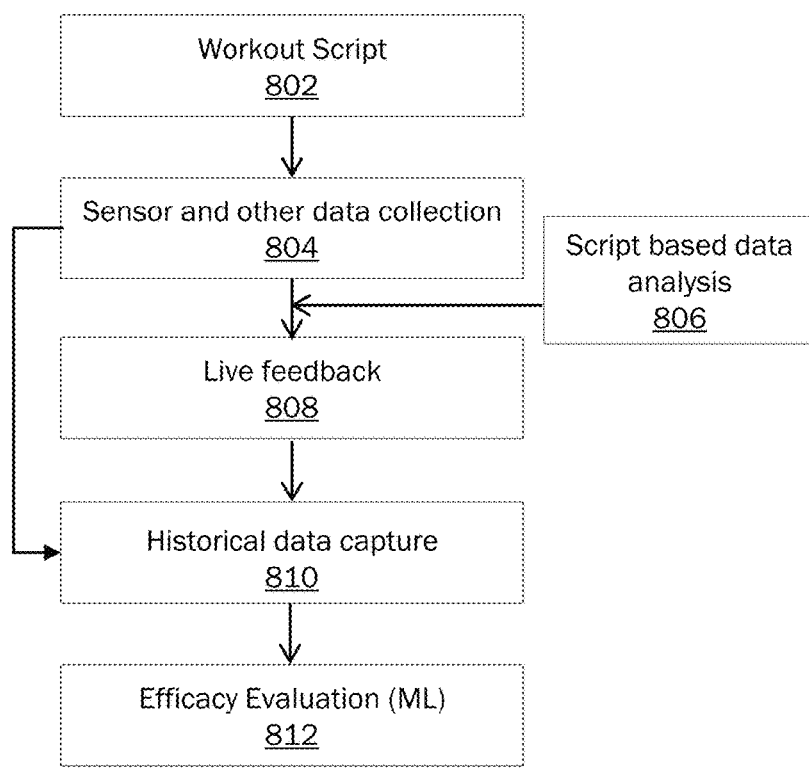
FIG. 8 illustrates use in conjunction with a workout script.

FIG. 8 illustrates use of system 800 in conjunction with a workout script that allows for individualized exercise routines that can be dynamically modified. A workout script 802 is provided. Based on sensor and other data collected 804, along with script-based data analysis 806, live feedback or adjustments to force profiles or exercise routine parameters (step 808) can be made. Historical data 810 is captured directly from sensors 804 or live feedback systems 808. This data can be used for live or offline machine learning supported user feedback, efficacy evaluation, and modification of routines and routine parameters 812.

Figure 9:
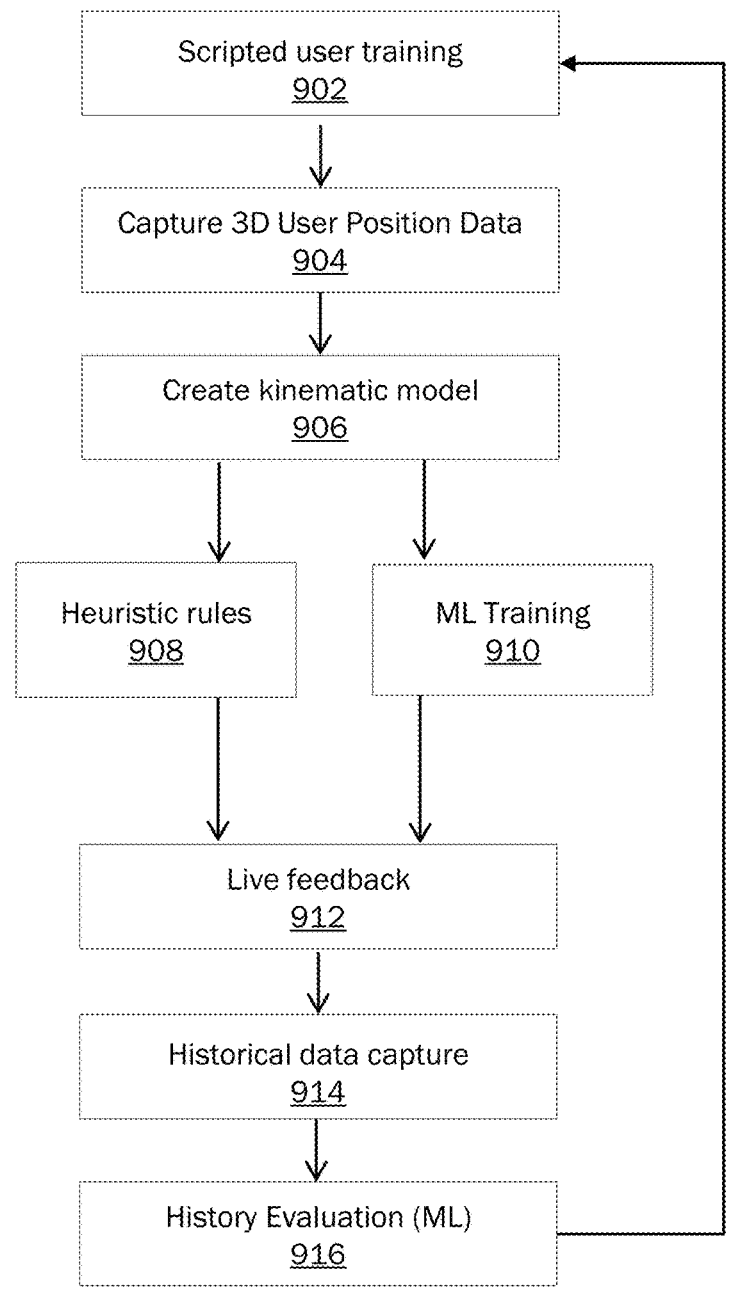
FIG. 9 illustrates operation with real-time live feedback.

FIG. 9 illustrates use of a system 900 with scripted user training 902 supported by real-time live feedback. Three-dimensional user position data is captured (step 904) and a kinematic model (step 906) created. Using one or both of heuristic rules (step 908) or trained machine learning systems (step 910), live feedback (step 912) is provided to the user. Historical data (step 914) is captured, evaluated using machine learning systems (step 916), and the results used to modify the exercise script.

Figure 10A:
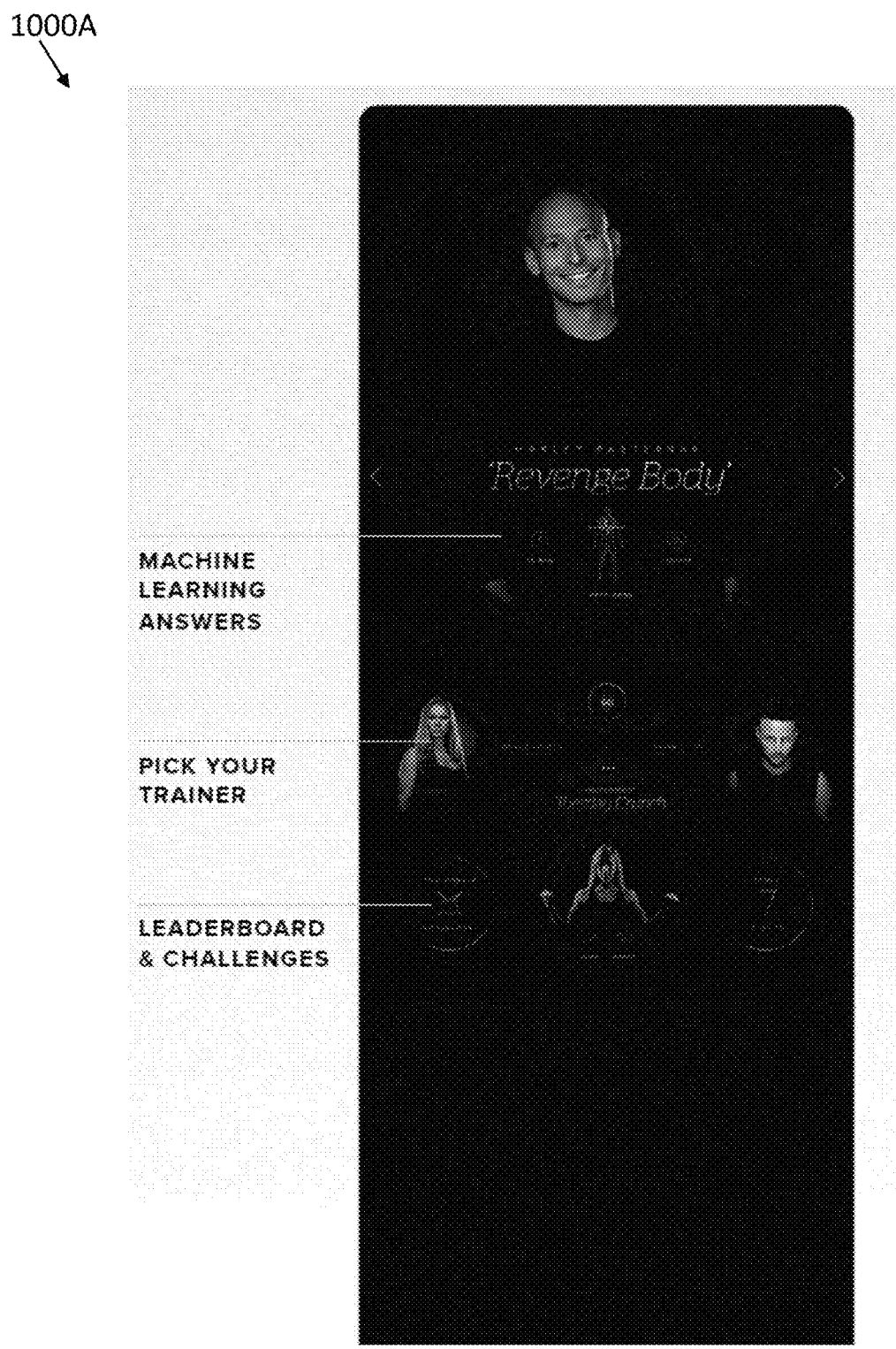
FIG. 10A-B illustrates representative user interface displays and functionality.
Figure 10B:
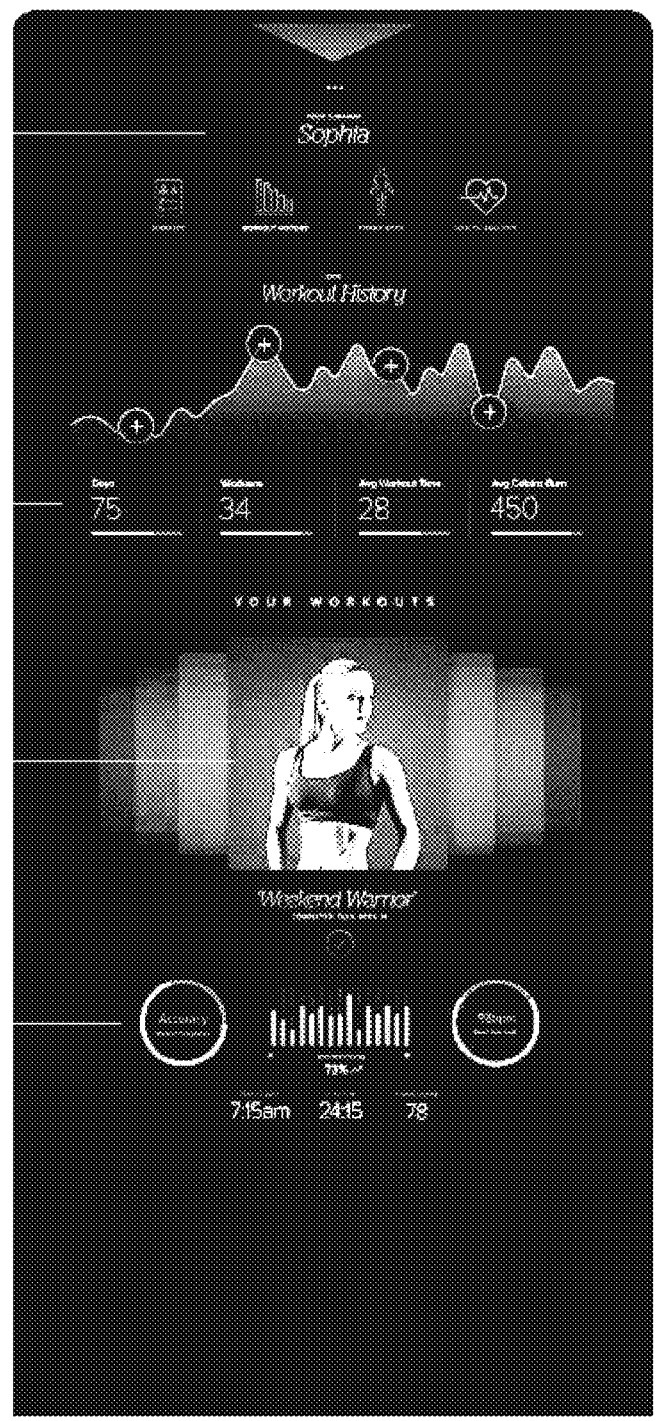

FIGS. 10A and 10B illustrates representative user interface displays. FIG. 10A illustrates a mirrored presentation of a user's face, with machine learned data, trainer selection options, and use data such as social networking-based leaderboards and challenges also being presented. Leaderboards can be live from people doing a workout session at the same time, or dynamically generated based on combination of user data and data from other user data. Other use data can be global or selected based on geography, user data, social network data, group, demographic data, or other groupings. FIG. 10B illustrates a personal profile, workout history with targets to encourage and push user exercise numbers, adaptive program selection, and real-time data. With the exception of the mirrored user face presentation, the illustrated data of FIGS. 10A-B can also be available for viewing on desktop computers, laptops, tablets or smartphones. In some embodiments, this data and can also be supplied in audio form. Selection of option can be through touchscreen, gestures, typed input, wired and wireless input devices or verbal instructions.

In the foregoing description, reference is made to the accompanying drawings that form a part thereof, and in which is shown by way of illustration specific exemplary embodiments in which the disclosure may be practiced. These embodiments are described in sufficient detail to enable those skilled in the art to practice the concepts disclosed herein, and it is to be understood that modifications to the various disclosed embodiments may be made, and other embodiments may be utilized, without departing from the scope of the present disclosure. The foregoing detailed description is, therefore, not to be taken in a limiting sense.

Reference throughout this specification to "one embodiment," "an embodiment," "one example," or "an example" means that a particular feature, structure, or characteristic described in connection with the embodiment or example is included in at least one embodiment of the present disclosure. Thus, appearances of the phrases "in one embodiment," "in an embodiment," "one example," or "an example" in various places throughout this specification are not necessarily all referring to the same embodiment or example. Furthermore, the particular features, structures, databases, or characteristics may be combined in any suitable combinations and/or sub-combinations in one or more embodiments or examples. In addition, it should be appreciated that the figures provided herewith are for explanation purposes to persons ordinarily skilled in the art and that the drawings are not necessarily drawn to scale.

Embodiments in accordance with the present disclosure may be embodied as an apparatus, method, or computer program product. Accordingly, the present disclosure may take the form of an entirely hardware-comprised embodiment, an entirely software-comprised embodiment (including firmware, resident software, micro-code, etc.), or an embodiment combining software and hardware aspects that may all generally be referred to herein as a "circuit," "module," or "system." Furthermore, embodiments of the present disclosure may take the form of a computer program product embodied in any tangible medium of expression having computer-usable program code embodied in the medium.

Any combination of one or more computer-usable or computer-readable media may be utilized. For example, a computer-readable medium may include one or more of a portable computer diskette, a hard disk, a random access memory (RAM) device, a read-only memory (ROM) device, an erasable programmable read-only memory (EPROM or Flash memory) device, a portable compact disc read-only memory (CDROM), an optical storage device, and a magnetic storage device. Computer program code for carrying out operations of the present disclosure may be written in any combination of one or more programming languages. Such code may be compiled from source code to computer-readable assembly language or machine code suitable for the device or computer on which the code will be executed.

Embodiments may also be implemented in cloud computing environments. In this description and the following claims, "cloud computing" may be defined as a model for enabling ubiquitous, convenient, on-demand network access to a shared pool of configurable computing resources (e.g., networks, servers, storage, applications, and services) that can be rapidly provisioned via virtualization and released with minimal management effort or service provider interaction and then scaled accordingly. A cloud model can be composed of various characteristics (e.g., on-demand self-service, broad network access, resource pooling, rapid elasticity, and measured service), service models (e.g., Software as a Service ("SaaS"), Platform as a Service ("PaaS"), and Infrastructure as a Service ("IaaS")), and deployment models (e.g., private cloud, community cloud, public cloud, and hybrid cloud).

The flow diagrams and block diagrams in the attached figures illustrate the architecture, functionality, and operation of possible implementations of systems, methods, and computer program products according to various embodiments of the present disclosure. In this regard, each block in the flow diagrams or block diagrams may represent a module, segment, or portion of code, which comprises one or more executable instructions for implementing the specified logical function(s). It will also be noted that each block of the block diagrams and/or flow diagrams, and combinations of blocks in the block diagrams and/or flow diagrams, may be implemented by special purpose hardware-based systems that perform the specified functions or acts, or combinations of special purpose hardware and computer instructions. These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flow diagram and/or block diagram block or blocks. Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims. It is also understood that other embodiments of this invention may be practiced in the absence of an element/step not specifically disclosed herein.

The invention claimed is:

1. An interactive exercise system comprising:
a mechanical support system;
a display module held by the mechanical support system and having a front side and a back side;
a mirror element attached to the display module and configured to at least partially cover the display module;
at least one movable arm;
at least one force-controlled component engageable by a user, via the at least one movable arm, and connected to the mechanical support system; and
a multi-axis hinge assembly coupling the at least one movable arm to the mechanical support system and enabling lateral and vertical pivoting of the at least one movable arm;

wherein the multi-axis hinge assembly enables pivoting of the at least one movable arm both in (a) an operable position such that the at least one movable arm protrudes forwardly from the front side of the display module and (b) a stowed position such that the least one movable arm is positioned over the back side of the display module, behind the mirror element and does not protrude from a perimeter of the back side of the display module.

2. The interactive exercise system of claim 1, wherein the display module provides video.

3. The interactive exercise system of claim 1, further comprising a three-dimensional camera system directed to monitor user position.

4. The interactive exercise system of claim 1, wherein the display module provides interactive graphics based at least in part on data provided through a three-dimensional camera.

5. The interactive exercise system of claim 1, wherein force applied to the user through the force-controlled component is based at least in part on user input.

6. The interactive exercise system of claim 1, wherein force applied to the user through the force-controlled component is based at least in part on detected user force input.

7. The interactive exercise system of claim 1, wherein force applied to the user through the force-controlled component is based at least in part on real time analysis of at least one of user position, user applied force, and user biometric signals.

8. The interactive exercise system of claim 1, further comprising a biometric signal analysis module able to detect at least one of heart rate and breath rate.

9. The interactive exercise system of claim 1, wherein the interactive exercise system allows selection of specific exercises from an exercise catalog module.

10. The interactive exercise system of claim 1, wherein the interactive exercise system stores exercise history in a personal exercise history module, the exercise history including at least one of three-dimensional user pose, video of user, and skeletal or joint extraction data.

11. The interactive exercise system of claim 1, further comprising an audio module to allow at least one of user voice control, receipt of audio instructions by a user, and music.

12. The interactive exercise system of claim 1, wherein the force-controlled component comprises:
 a reel mounted to the mechanical support system;
 a motor coupled to the reel;
 a pulley assembly incorporating a force sensor;
 a graspable handle; and
 a cord extending from the reel, through the pulley assembly, through the at least one movable arm, and connected to the graspable handle.

13. An interactive exercise system comprising:
 a mechanical support system;
 a display module held by the mechanical support system;
 a mirror element attached to at least partially cover the display module;
 at least one movable arm;
 at least one force-controlled component engageable by a user, via the at least one movable arm, and connected to the mechanical support system; and
 a multi-axis hinge assembly coupling the at least one movable arm to the mechanical support system and enabling lateral and vertical pivoting of the at least one movable arm, the multi-axis hinge assembly comprising:
 a rotational arm mechanism coupled to the at least one movable arm; and
 a hinge plate mechanism, the rotational arm mechanism being slidably connected to the hinge plate mechanism.

* * * * *